United States Patent
Khairkhahan

(10) Patent No.: US 12,408,917 B2
(45) Date of Patent: Sep. 9, 2025

(54) METHODS AND DEVICES FOR VALVE CLIP EXCISION

(71) Applicant: Evalve, Inc., Santa Clara, CA (US)

(72) Inventor: Alex Khairkhahan, Palo Alto, CA (US)

(73) Assignee: EVALVE, INC., Santa Clara, CA (US)

(*) Notice: Subject to any disclaimer, the term of this patent is extended or adjusted under 35 U.S.C. 154(b) by 603 days.

(21) Appl. No.: 16/916,754

(22) Filed: Jun. 30, 2020

(65) Prior Publication Data

US 2020/0323528 A1 Oct. 15, 2020

Related U.S. Application Data

(62) Division of application No. 15/642,245, filed on Jul. 5, 2017, now Pat. No. 10,736,632.

(Continued)

(51) Int. Cl.
*A61B 17/10* (2006.01)
*A61B 17/128* (2006.01)
(Continued)

(52) U.S. Cl.
CPC .......... *A61B 17/10* (2013.01); *A61B 17/1285* (2013.01); *A61B 17/320016* (2013.01);
(Continued)

(58) Field of Classification Search
CPC ........ A61B 17/320016; A61B 17/3205; A61B 17/10; A61B 17/1285; A61B 17/083;
(Continued)

(56) References Cited

U.S. PATENT DOCUMENTS

| 1,996,261 A | 4/1935 | Storz |
| 2,097,018 A | 10/1937 | Chamberlin |

(Continued)

FOREIGN PATENT DOCUMENTS

| CN | 1469724 | 1/2004 |
| CN | 102770080 | 11/2012 |

(Continued)

OTHER PUBLICATIONS

Nishimura, et al. 2014 AHA/ACC guideline for the management of patients with valvular heart disease: executive summary: a report of the American College of Cardiology/American Heart Association Task Force on Practice Guidelines. J Am Coll Cardiol. Jun. 10, 2014; 63(22):2438-88.

(Continued)

*Primary Examiner* — Anh T Dang
(74) *Attorney, Agent, or Firm* — Workman Nydegger

(57) ABSTRACT

A system for excising an implanted clip approximating opposed valve leaflets in a heart valve includes a capture catheter configured to be introduced proximate the valve leaflets on one side of the clip, a transfer catheter configured to be introduced proximate the valve leaflets on another side of the clip, and a cutting tool configured to be deployed between the capture and transfer catheters and to be engaged against tissue of at least one of the valve leaflets and to excise the clip. A removal catheter may optionally be used to remove the clip from the heart.

21 Claims, 21 Drawing Sheets

Related U.S. Application Data

(60) Provisional application No. 62/418,571, filed on Nov. 7, 2016, provisional application No. 62/359,121, filed on Jul. 6, 2016.

(51) Int. Cl.
| | |
|---|---|
| *A61B 17/32* | (2006.01) |
| *A61B 17/3205* | (2006.01) |
| *A61B 18/14* | (2006.01) |
| A61B 17/00 | (2006.01) |
| A61B 17/08 | (2006.01) |
| A61B 17/22 | (2006.01) |
| A61B 18/00 | (2006.01) |
| A61F 2/24 | (2006.01) |

(52) U.S. Cl.
CPC ...... *A61B 17/3205* (2013.01); *A61B 18/1492* (2013.01); *A61B 2017/00243* (2013.01); *A61B 2017/00358* (2013.01); *A61B 2017/00783* (2013.01); *A61B 2017/00876* (2013.01); *A61B 17/083* (2013.01); *A61B 2017/22035* (2013.01); *A61B 2017/32006* (2013.01); *A61B 2018/00369* (2013.01); *A61B 2018/00601* (2013.01); *A61B 2018/1407* (2013.01); *A61B 2018/144* (2013.01); *A61F 2/246* (2013.01); *A61F 2/2466* (2013.01)

(58) Field of Classification Search
CPC ........... A61B 2017/00243; A61B 2017/00783; A61B 2017/32006; A61B 2017/22035; A61B 2017/00876; A61B 2017/00358; A61B 18/1492; A61B 2018/144; A61B 2018/1407; A61B 2018/00601; A61B 2018/00369; A61F 2/2466; A61F 2/246
See application file for complete search history.

(56) References Cited

U.S. PATENT DOCUMENTS

| | | |
|---|---|---|
| 2,108,206 A | 2/1938 | Meeker |
| 3,296,668 A | 1/1967 | Aiken |
| 3,378,010 A | 4/1968 | Codling et al. |
| 3,470,875 A | 10/1969 | Johnson et al. |
| 3,557,780 A | 1/1971 | Sato |
| 3,671,979 A | 6/1972 | Moulopoulos |
| 3,675,639 A | 7/1972 | Cimber |
| 3,776,237 A | 12/1973 | Hill et al. |
| 3,874,338 A | 4/1975 | Happel |
| 3,874,388 A | 4/1975 | King et al. |
| 4,007,743 A | 2/1977 | Blake |
| 4,056,854 A | 11/1977 | Boretos et al. |
| 4,064,881 A | 12/1977 | Meredith |
| 4,091,815 A | 5/1978 | Larsen |
| 4,112,951 A | 9/1978 | Hulka et al. |
| 4,235,238 A | 11/1980 | Ogiu et al. |
| 4,297,749 A | 11/1981 | Davis et al. |
| 4,312,337 A | 1/1982 | Donahue |
| 4,425,908 A | 1/1984 | Simon |
| 4,458,682 A | 7/1984 | Cerwin |
| 4,484,579 A | 11/1984 | Meno et al. |
| 4,487,205 A | 12/1984 | Di Giovanni et al. |
| 4,498,476 A | 2/1985 | Cerwin et al. |
| 4,510,934 A | 4/1985 | Batra |
| 4,531,522 A | 7/1985 | Bedi et al. |
| 4,578,061 A | 3/1986 | Lemelson |
| 4,641,366 A | 2/1987 | Yokoyama et al. |
| 4,686,965 A | 8/1987 | Bonnet et al. |
| 4,777,951 A | 10/1988 | Cribier et al. |
| 4,809,695 A | 3/1989 | Gwathmey et al. |
| 4,872,455 A | 10/1989 | Pinchuk et al. |
| 4,878,495 A | 11/1989 | Grayzel |
| 4,917,089 A | 4/1990 | Sideris |
| 4,944,295 A | 7/1990 | Gwathmey et al. |
| 4,969,890 A | 11/1990 | Sugita et al. |
| 4,994,077 A | 2/1991 | Dobben |
| 5,015,249 A | 5/1991 | Nakao et al. |
| 5,019,096 A | 5/1991 | Fox et al. |
| 5,042,707 A | 8/1991 | Taheri |
| 5,047,041 A | 9/1991 | Samuels |
| 5,049,153 A | 9/1991 | Nakao et al. |
| 5,053,043 A | 10/1991 | Gottesman et al. |
| 5,061,277 A | 10/1991 | Carpentier et al. |
| 5,069,679 A | 12/1991 | Taheri |
| 5,071,428 A | 12/1991 | Chin |
| 5,078,722 A | 1/1992 | Stevens |
| 5,078,723 A | 1/1992 | Dance et al. |
| 5,108,368 A | 4/1992 | Hammerslag et al. |
| 5,125,758 A | 6/1992 | Dewan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,217,460 A | 6/1993 | Knoepfler |
| 5,226,429 A | 7/1993 | Kuzmak |
| 5,226,911 A | 7/1993 | Chee et al. |
| 5,234,437 A | 8/1993 | Sepetka |
| 5,242,456 A | 9/1993 | Nash et al. |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,271,381 A | 12/1993 | Ailinger et al. |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A | 6/1994 | Heidmueller |
| 5,325,845 A | 7/1994 | Adair |
| 5,330,442 A | 7/1994 | Green et al. |
| 5,332,402 A | 7/1994 | Teitelbaum |
| 5,336,227 A | 8/1994 | Nakao et al. |
| 5,342,393 A | 8/1994 | Stack |
| 5,350,397 A | 9/1994 | Palermo et al. |
| 5,350,399 A | 9/1994 | Erlebacher et al. |
| 5,359,994 A | 11/1994 | Krauter et al. |
| 5,368,564 A | 11/1994 | Savage |
| 5,368,601 A | 11/1994 | Sauer et al. |
| 5,373,854 A | 12/1994 | Kolozsi |
| 5,383,886 A | 1/1995 | Kensey et al. |
| 5,387,219 A | 2/1995 | Rappe |
| 5,391,182 A | 2/1995 | Chin |
| 5,395,030 A | 3/1995 | Kuramoto et al. |
| 5,403,312 A | 4/1995 | Yates et al. |
| 5,403,326 A | 4/1995 | Harrison et al. |
| 5,411,552 A | 5/1995 | Andersen et al. |
| 5,417,684 A | 5/1995 | Jackson et al. |
| 5,417,699 A | 5/1995 | Klein et al. |
| 5,417,700 A | 5/1995 | Egan |
| 5,423,830 A | 6/1995 | Schneebaum et al. |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,472,423 A | 12/1995 | Gronauer |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |

(56) References Cited

U.S. PATENT DOCUMENTS

| | | |
|---|---|---|
| 5,487,746 A | 1/1996 | Yu et al. |
| 5,496,332 A | 3/1996 | Sierra et al. |
| 5,507,725 A | 4/1996 | Savage et al. |
| 5,507,755 A | 4/1996 | Gresl et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,562,678 A | 10/1996 | Booker |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,584,803 A | 12/1996 | Stevens et al. |
| 5,593,424 A | 1/1997 | Northrup III |
| 5,593,435 A | 1/1997 | Carpentier et al. |
| 5,609,598 A | 3/1997 | Laufer et al. |
| 5,617,854 A | 4/1997 | Anand |
| 5,618,306 A | 4/1997 | Roth et al. |
| 5,620,452 A | 4/1997 | Yoon |
| 5,620,461 A | 4/1997 | Muijs Van De Moer et al. |
| 5,626,588 A | 5/1997 | Sauer et al. |
| 5,634,932 A | 6/1997 | Schmidt |
| 5,636,634 A | 6/1997 | Kordis et al. |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,669,919 A | 9/1997 | Sanders et al. |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keita et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racenet et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,271 A | 4/1998 | Nakao et al. |
| 5,741,280 A | 4/1998 | Fleenor |
| 5,746,747 A | 5/1998 | McKeating |
| 5,749,828 A | 5/1998 | Solomon et al. |
| 5,759,193 A | 6/1998 | Burbank et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A | 9/1998 | Kontos |
| 5,810,853 A | 9/1998 | Yoon |
| 5,810,876 A | 9/1998 | Kelleher |
| 5,814,029 A | 9/1998 | Hassett |
| 5,820,591 A | 10/1998 | Thompson et al. |
| 5,820,592 A | 10/1998 | Hammerslag |
| 5,820,630 A | 10/1998 | Lind |
| 5,820,631 A | 10/1998 | Nobles |
| 5,823,955 A | 10/1998 | Kuck et al. |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,843,103 A | 12/1998 | Wulfman |
| 5,849,019 A | 12/1998 | Yoon |
| 5,853,422 A | 12/1998 | Huebsch et al. |
| 5,855,271 A | 1/1999 | Eubanks et al. |
| 5,855,590 A | 1/1999 | Malecki et al. |
| 5,855,614 A | 1/1999 | Stevens et al. |
| 5,860,990 A | 1/1999 | Nobles et al. |
| 5,861,003 A | 1/1999 | Latson et al. |
| 5,868,733 A | 2/1999 | Ockuly et al. |
| 5,876,399 A | 3/1999 | Chia et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,895,404 A | 4/1999 | Ruiz |
| 5,895,417 A | 4/1999 | Pomeranz et al. |
| 5,906,620 A | 5/1999 | Nakao et al. |
| 5,908,420 A | 6/1999 | Parins |
| 5,916,147 A | 6/1999 | Boury |
| 5,928,224 A | 7/1999 | Laufer |
| 5,944,733 A | 8/1999 | Engelson |
| 5,947,363 A | 9/1999 | Bolduc et al. |
| 5,954,732 A | 9/1999 | Hart et al. |
| 5,957,949 A | 9/1999 | Leonhard et al. |
| 5,957,973 A | 9/1999 | Quiachon et al. |
| 5,972,020 A | 10/1999 | Carpentier et al. |
| 5,972,030 A | 10/1999 | Garrison et al. |
| 5,980,455 A | 11/1999 | Daniel et al. |
| 5,989,284 A | 11/1999 | Laufer |
| 5,997,547 A | 12/1999 | Nakao et al. |
| 6,007,546 A | 12/1999 | Snow et al. |
| 6,015,417 A | 1/2000 | Reynolds, Jr. |
| 6,019,722 A | 2/2000 | Spence et al. |
| 6,022,360 A | 2/2000 | Reimels et al. |
| 6,033,378 A | 3/2000 | Lundquist et al. |
| 6,033,419 A | 3/2000 | Hamblin et al. |
| 6,036,699 A | 3/2000 | Andreas et al. |
| 6,048,351 A | 4/2000 | Gordon et al. |
| 6,053,933 A | 4/2000 | Balazs et al. |
| 6,056,769 A | 5/2000 | Epstein et al. |
| 6,059,757 A | 5/2000 | Macoviak et al. |
| 6,060,628 A | 5/2000 | Aoyama et al. |
| 6,060,629 A | 5/2000 | Pham et al. |
| 6,063,106 A | 5/2000 | Gibson |
| 6,066,146 A | 5/2000 | Carroll et al. |
| 6,068,628 A | 5/2000 | Fanton et al. |
| 6,068,629 A | 5/2000 | Haissaguerre et al. |
| 6,077,214 A | 6/2000 | Mortier et al. |
| 6,086,600 A | 7/2000 | Kortenbach |
| 6,088,889 A | 7/2000 | Luther et al. |
| 6,090,118 A | 7/2000 | McGuckin, Jr. |
| 6,099,505 A | 8/2000 | Ryan et al. |
| 6,099,553 A | 8/2000 | Hart et al. |
| 6,110,145 A | 8/2000 | Macoviak |
| 6,117,144 A | 9/2000 | Nobles et al. |
| 6,117,159 A | 9/2000 | Huebsch et al. |
| 6,123,665 A | 9/2000 | Kawano |
| 6,123,699 A | 9/2000 | Webster, Jr. |
| 6,126,658 A | 10/2000 | Baker |
| 6,132,447 A | 10/2000 | Dorsey |
| 6,136,010 A | 10/2000 | Modesitt et al. |
| 6,139,508 A | 10/2000 | Simpson |
| 6,143,024 A | 11/2000 | Campbell et al. |
| 6,159,240 A | 12/2000 | Sparer et al. |
| 6,162,233 A | 12/2000 | Williamson, IV et al. |
| 6,165,164 A | 12/2000 | Hill et al. |
| 6,165,183 A | 12/2000 | Kuehn et al. |
| 6,165,204 A | 12/2000 | Levinson et al. |
| 6,168,614 B1 | 1/2001 | Andersen et al. |
| 6,171,320 B1 | 1/2001 | Monassevitch |
| 6,174,322 B1 | 1/2001 | Schneidt |
| 6,180,059 B1 | 1/2001 | Divino, Jr. et al. |

(56) References Cited

U.S. PATENT DOCUMENTS

| | | |
|---|---|---|
| 6,182,664 B1 | 2/2001 | Cosgrove |
| 6,187,003 B1 | 2/2001 | Buysse et al. |
| 6,190,408 B1 | 2/2001 | Melvin |
| 6,197,043 B1 | 3/2001 | Davidson |
| 6,203,531 B1 | 3/2001 | Ockuly et al. |
| 6,203,553 B1 | 3/2001 | Robertson et al. |
| 6,206,893 B1 | 3/2001 | Klein et al. |
| 6,206,907 B1 | 3/2001 | Marino et al. |
| 6,210,419 B1 | 4/2001 | Mayenberger et al. |
| 6,210,432 B1 | 4/2001 | Solem et al. |
| 6,245,079 B1 | 6/2001 | Nobles et al. |
| 6,264,617 B1 | 7/2001 | Bales et al. |
| 6,267,746 B1 | 7/2001 | Bumbalough |
| 6,267,781 B1 | 7/2001 | Tu |
| 6,269,819 B1 | 8/2001 | Oz et al. |
| 6,277,555 B1 | 8/2001 | Duran et al. |
| 6,283,127 B1 | 9/2001 | Sterman et al. |
| 6,283,962 B1 | 9/2001 | Tu et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,334,860 B1 | 1/2002 | Dorn |
| 6,352,708 B1 | 3/2002 | Duran et al. |
| 6,355,030 B1 | 3/2002 | Aldrich et al. |
| 6,358,277 B1 | 3/2002 | Duran |
| 6,368,326 B1 | 4/2002 | Dakin et al. |
| 6,387,104 B1 | 5/2002 | Pugsley, Jr. et al. |
| 6,402,780 B2 | 6/2002 | Williamson et al. |
| 6,402,781 B1 | 6/2002 | Langberg et al. |
| 6,406,420 B1 | 6/2002 | McCarthy et al. |
| 6,419,640 B1 | 7/2002 | Taylor |
| 6,419,669 B1 | 7/2002 | Frazier et al. |
| 6,461,366 B1 | 10/2002 | Seguin |
| 6,464,707 B1 | 10/2002 | Bjerken |
| 6,482,224 B1 | 11/2002 | Michler et al. |
| 6,485,489 B2 | 11/2002 | Teirstein et al. |
| 6,494,881 B1 | 12/2002 | Bales et al. |
| 6,508,828 B1 | 1/2003 | Akerfeldt et al. |
| 6,517,550 B1 | 2/2003 | Konya et al. |
| 6,533,796 B1 | 3/2003 | Sauer et al. |
| 6,537,314 B2 | 3/2003 | Langberg et al. |
| 6,540,755 B2 | 4/2003 | Ockuly et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,921 B2 | 9/2003 | Blatter et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,669,687 B1 | 12/2003 | Saadat |
| 6,685,648 B2 | 2/2004 | Flaherty et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,825 B2 | 3/2004 | Frazier et al. |
| 6,702,826 B2 | 3/2004 | Liddicoat et al. |
| 6,709,382 B1 | 3/2004 | Homer |
| 6,709,456 B2 | 3/2004 | Langberg et al. |
| 6,718,985 B2 | 4/2004 | Hlavka et al. |
| 6,719,767 B1 | 4/2004 | Kimblad |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,860,179 B2 | 3/2005 | Hopper et al. |
| 6,875,224 B2 | 4/2005 | Grimes |
| 6,926,715 B1 | 8/2005 | Hauck et al. |
| 6,932,810 B2 | 8/2005 | Ryan |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,004,970 B2 | 2/2006 | Cauthen III et al. |
| 7,011,669 B2 | 3/2006 | Kimblad |
| 7,033,390 B2 | 4/2006 | Johnson et al. |
| 7,048,754 B2 | 5/2006 | Martin et al. |
| 7,056,294 B2 | 6/2006 | Khairkhahan et al. |
| 7,112,207 B2 | 9/2006 | Allen et al. |
| 7,226,467 B2 | 6/2007 | Lucatero et al. |
| 7,258,694 B1 | 8/2007 | Choi et al. |
| 7,288,097 B2 | 10/2007 | Seguin |
| 7,291,168 B2 | 11/2007 | Macoviak et al. |
| 7,338,467 B2 | 3/2008 | Lutter |
| 7,381,210 B2 | 6/2008 | Zarbatany et al. |
| 7,435,257 B2 | 10/2008 | Lashinski et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,604,646 B2 | 10/2009 | Goldfarb et al. |
| 7,608,091 B2 | 10/2009 | Goldfarb et al. |
| 7,635,329 B2 | 12/2009 | Goldfarb et al. |
| 7,651,502 B2 | 1/2010 | Jackson |
| 7,655,015 B2 | 2/2010 | Goldfarb et al. |
| 7,666,204 B2 | 2/2010 | Thornton et al. |
| 7,955,340 B2 | 6/2011 | Michlitsch |
| 8,216,234 B2 | 7/2012 | Long |
| 8,257,356 B2 | 9/2012 | Bleich et al. |
| 8,398,708 B2 | 3/2013 | Meiri et al. |
| 8,435,237 B2 | 5/2013 | Bahney |
| 8,496,655 B2 * | 7/2013 | Epp .................... A61B 18/14 606/45 |
| 8,500,768 B2 | 8/2013 | Cohen |
| 8,523,881 B2 | 9/2013 | Cabiri et al. |
| 8,623,077 B2 | 1/2014 | Cohn |
| 8,690,858 B2 | 4/2014 | Machold et al. |
| 8,821,518 B2 | 9/2014 | Saliman et al. |
| 8,926,588 B2 | 1/2015 | Berthiaume et al. |
| 9,126,032 B2 | 9/2015 | Khairkhahan et al. |
| 9,211,119 B2 | 12/2015 | Hendricksen |
| 9,370,341 B2 | 6/2016 | Ceniccola et al. |
| 9,498,331 B2 | 11/2016 | Chang et al. |
| 9,572,666 B2 | 2/2017 | Basude et al. |
| 9,770,256 B2 | 9/2017 | Cohen et al. |
| 9,949,833 B2 | 4/2018 | McCleary et al. |
| 10,238,493 B1 | 3/2019 | Metchik et al. |
| 10,667,804 B2 | 6/2020 | Basude et al. |
| 11,013,554 B2 | 5/2021 | Coates |
| 11,406,250 B2 | 8/2022 | Saadat et al. |
| 2001/0002445 A1 | 5/2001 | Vesely |
| 2001/0004715 A1 | 6/2001 | Duran et al. |
| 2001/0005787 A1 | 6/2001 | Oz et al. |
| 2001/0010005 A1 | 7/2001 | Kammerer et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2001/0044635 A1 | 11/2001 | Niizeki et al. |
| 2002/0013547 A1 | 1/2002 | Paskar |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |

(56) References Cited

U.S. PATENT DOCUMENTS

| | | |
|---|---|---|
| 2002/0055767 A1 | 5/2002 | Forde et al. |
| 2002/0055774 A1 | 5/2002 | Liddicoat |
| 2002/0055775 A1 | 5/2002 | Carpentier et al. |
| 2002/0058910 A1 | 5/2002 | Hermann et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hilavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0173811 A1 | 11/2002 | Tu et al. |
| 2002/0173841 A1 | 11/2002 | Ortiz et al. |
| 2002/0183766 A1 | 12/2002 | Seguin |
| 2002/0183787 A1 | 12/2002 | Wahr et al. |
| 2002/0183835 A1 | 12/2002 | Taylor et al. |
| 2003/0005797 A1 | 1/2003 | Hopper et al. |
| 2003/0045778 A1 | 3/2003 | Ohline et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0015232 A1 | 1/2004 | Shu et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030319 A1 | 2/2004 | Korkor et al. |
| 2004/0030382 A1 | 2/2004 | St. Goar et al. |
| 2004/0034380 A1 | 2/2004 | Woolfson et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0059345 A1 | 3/2004 | Nakao et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092858 A1 | 5/2004 | Wilson et al. |
| 2004/0092962 A1 | 5/2004 | Thornton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0116848 A1 | 6/2004 | Gardeski et al. |
| 2004/0116951 A1 | 6/2004 | Rosengart |
| 2004/0122448 A1 | 6/2004 | Levine |
| 2004/0127849 A1 | 7/2004 | Kantor |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133232 A1 | 7/2004 | Rosenbluth et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0147826 A1 | 7/2004 | Peterson |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0167539 A1 | 8/2004 | Kuehn et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225233 A1 | 11/2004 | Frankowski et al. |
| 2004/0225300 A1 | 11/2004 | Goldfarb et al. |
| 2004/0225305 A1 | 11/2004 | Ewers et al. |
| 2004/0225353 A1* | 11/2004 | McGuckin, Jr. ...... A61F 2/2421 623/2.11 |
| 2004/0236354 A1 | 11/2004 | Seguin |
| 2004/0242960 A1 | 12/2004 | Orban |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2004/0260393 A1 | 12/2004 | Randert et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goer et al. |
| 2005/0021057 A1 | 1/2005 | St. Goer et al. |
| 2005/0021058 A1 | 1/2005 | Negro |
| 2005/0033446 A1 | 2/2005 | Deem et al. |
| 2005/0038383 A1 | 2/2005 | Kelley et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0065453 A1 | 3/2005 | Shabaz et al. |
| 2005/0085903 A1 | 4/2005 | Lau |
| 2005/0119735 A1 | 6/2005 | Spence et al. |
| 2005/0131438 A1 | 6/2005 | Cohn |
| 2005/0143809 A1 | 6/2005 | Salahieh et al. |
| 2005/0149014 A1 | 7/2005 | Hauck et al. |
| 2005/0159763 A1 | 7/2005 | Mollenauer |
| 2005/0159810 A1 | 7/2005 | Filsoufi |
| 2005/0192633 A1 | 9/2005 | Montpetit |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0256452 A1 | 11/2005 | DeMarchi et al. |
| 2005/0267493 A1 | 12/2005 | Schreck et al. |
| 2005/0273160 A1 | 12/2005 | Lashinski et al. |
| 2005/0277876 A1 | 12/2005 | Hayden |
| 2005/0287493 A1 | 12/2005 | Novak et al. |
| 2006/0004247 A1 | 1/2006 | Kute et al. |
| 2006/0009759 A1 | 1/2006 | Christian et al. |
| 2006/0015003 A1 | 1/2006 | Moaddes et al. |
| 2006/0015179 A1 | 1/2006 | Bulman-Fleming et al. |
| 2006/0020275 A1 | 1/2006 | Goldfarb et al. |
| 2006/0020327 A1 | 1/2006 | Lashinski et al. |
| 2006/0020334 A1 | 1/2006 | Lashinski et al. |
| 2006/0030866 A1 | 2/2006 | Schreck |
| 2006/0030867 A1 | 2/2006 | Zadno |
| 2006/0030885 A1 | 2/2006 | Hyde |

(56) References Cited

U.S. PATENT DOCUMENTS

| | | |
|---|---|---|
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0074484 A1 | 4/2006 | Huber |
| 2006/0089671 A1 | 4/2006 | Goldfarb et al. |
| 2006/0089711 A1 | 4/2006 | Dolan |
| 2006/0135961 A1 | 6/2006 | Rosenman et al. |
| 2006/0135993 A1 | 6/2006 | Seguin |
| 2006/0184198 A1 | 8/2006 | Bales |
| 2006/0184203 A1 | 8/2006 | Martin et al. |
| 2006/0195012 A1 | 8/2006 | Mortier et al. |
| 2006/0229708 A1 | 10/2006 | Powell et al. |
| 2006/0252984 A1 | 11/2006 | Randert et al. |
| 2006/0276890 A1 | 12/2006 | Solem et al. |
| 2007/0016225 A1 | 1/2007 | Nakao |
| 2007/0038293 A1 | 2/2007 | St. Goar et al. |
| 2007/0060997 A1 | 3/2007 | de Boer |
| 2007/0073185 A1 | 3/2007 | Nakao |
| 2007/0100356 A1 | 5/2007 | Lucatero et al. |
| 2007/0118155 A1 | 5/2007 | Goldfarb et al. |
| 2007/0129737 A1 | 6/2007 | Goldfarb et al. |
| 2007/0173757 A1 | 7/2007 | Levine et al. |
| 2007/0197858 A1 | 8/2007 | Goldfarb et al. |
| 2007/0198082 A1 | 8/2007 | Kapadia et al. |
| 2007/0260225 A1 | 11/2007 | Sakakine et al. |
| 2007/0287884 A1 | 12/2007 | Schena |
| 2008/0009858 A1 | 1/2008 | Rizvi |
| 2008/0039935 A1 | 2/2008 | Buch et al. |
| 2008/0045936 A1 | 2/2008 | Vaska et al. |
| 2008/0051703 A1 | 2/2008 | Thornton et al. |
| 2008/0051807 A1 | 2/2008 | St. Goar et al. |
| 2008/0097467 A1 | 4/2008 | Gruber et al. |
| 2008/0097489 A1 | 4/2008 | Goldfarb et al. |
| 2008/0167714 A1 | 7/2008 | St. Goer et al. |
| 2008/0183194 A1 | 7/2008 | Goldfarb et al. |
| 2008/0188850 A1 | 8/2008 | Mody et al. |
| 2008/0195126 A1 | 8/2008 | Solem |
| 2008/0243249 A1 | 10/2008 | Kohm et al. |
| 2008/0294175 A1 | 11/2008 | Bardsley et al. |
| 2008/0312496 A1 | 12/2008 | Zwolinski |
| 2009/0012538 A1 | 1/2009 | Saliman et al. |
| 2009/0036768 A1 | 2/2009 | Seehusen et al. |
| 2009/0156995 A1 | 6/2009 | Martin et al. |
| 2009/0163934 A1 | 6/2009 | Raschdorf, Jr. et al. |
| 2009/0177266 A1 | 7/2009 | Powell et al. |
| 2009/0192510 A1 | 7/2009 | Bahney |
| 2009/0198322 A1 | 8/2009 | Deem et al. |
| 2009/0204005 A1 | 8/2009 | Keast et al. |
| 2009/0209955 A1 | 8/2009 | Forster et al. |
| 2009/0209991 A1 | 8/2009 | Hinchliffe et al. |
| 2009/0270858 A1 | 10/2009 | Hauck et al. |
| 2009/0276039 A1 | 11/2009 | Meretei |
| 2009/0281619 A1 | 11/2009 | Le et al. |
| 2009/0326567 A1 | 12/2009 | Goldfarb et al. |
| 2010/0016958 A1 | 1/2010 | St. Goer et al. |
| 2010/0022823 A1 | 1/2010 | Goldfarb et al. |
| 2010/0044410 A1 | 2/2010 | Argentine et al. |
| 2010/0121437 A1 | 5/2010 | Subramanian et al. |
| 2010/0152612 A1 | 6/2010 | Headley et al. |
| 2010/0217261 A1 | 8/2010 | Watson |
| 2010/0262231 A1 | 10/2010 | Tuval et al. |
| 2010/0268226 A1 | 10/2010 | Epp et al. |
| 2010/0298929 A1 | 11/2010 | Thornton et al. |
| 2011/0009864 A1 | 1/2011 | Bucciaglia et al. |
| 2011/0184405 A1 | 7/2011 | Mueller |
| 2011/0224710 A1 | 9/2011 | Bleich |
| 2011/0238052 A1 | 9/2011 | Robinson |
| 2011/0282250 A1 | 11/2011 | Fung et al. |
| 2012/0022527 A1 | 1/2012 | Woodruff |
| 2012/0022640 A1 | 1/2012 | Gross et al. |
| 2012/0065464 A1 | 3/2012 | Ellis et al. |
| 2012/0150194 A1 | 6/2012 | Odermatt et al. |
| 2012/0157765 A1 | 6/2012 | Mitelberg |
| 2012/0172915 A1 | 7/2012 | Fifer et al. |
| 2012/0179184 A1 | 7/2012 | Orlov |
| 2012/0265222 A1 | 10/2012 | Gordin et al. |
| 2012/0310330 A1 | 12/2012 | Buchbinder et al. |
| 2012/0316639 A1 | 12/2012 | Kleinschrodt |
| 2012/0330348 A1 | 12/2012 | Strauss et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0109910 A1 | 5/2013 | Alexander et al. |
| 2013/0172828 A1 | 7/2013 | Kappel et al. |
| 2013/0317515 A1 | 11/2013 | Kuroda et al. |
| 2014/0039511 A1 | 2/2014 | Morris et al. |
| 2014/0135799 A1 | 5/2014 | Henderson |
| 2014/0228871 A1 | 8/2014 | Cohen et al. |
| 2014/0276913 A1 | 9/2014 | Tah et al. |
| 2014/0309670 A1 | 10/2014 | Bakos et al. |
| 2014/0324164 A1 | 10/2014 | Gross et al. |
| 2014/0350662 A1 | 11/2014 | Vaturi |
| 2014/0358224 A1 | 12/2014 | Tegels et al. |
| 2014/0364866 A1 | 12/2014 | Dryden et al. |
| 2014/0379074 A1 | 12/2014 | Spence et al. |
| 2015/0005704 A1 | 1/2015 | Heisel et al. |
| 2015/0005801 A1 | 1/2015 | Marquis et al. |
| 2015/0051698 A1 | 2/2015 | Ruyra Baliarda et al. |
| 2015/0094800 A1 | 4/2015 | Chawla |
| 2015/0112430 A1 | 4/2015 | Creaven et al. |
| 2015/0211946 A1 | 7/2015 | Pons et al. |
| 2015/0230947 A1 | 8/2015 | Krieger et al. |
| 2015/0257877 A1 | 9/2015 | Hernandez |
| 2015/0257883 A1 | 9/2015 | Basude et al. |
| 2015/0306806 A1 | 10/2015 | Dando et al. |
| 2015/0313581 A1 | 11/2015 | Wolfe et al. |
| 2016/0015410 A1 | 1/2016 | Asirvatham et al. |
| 2016/0074165 A1 | 3/2016 | Spence et al. |
| 2016/0174979 A1 | 6/2016 | Wei |
| 2016/0317174 A1 | 11/2016 | Dake |
| 2017/0042678 A1 | 2/2017 | Ganesan et al. |
| 2017/0100183 A1 | 4/2017 | Iaizzo et al. |
| 2017/0143330 A1 | 5/2017 | Basude et al. |
| 2017/0202559 A1 | 7/2017 | Taha |
| 2017/0232238 A1 | 8/2017 | Biller et al. |
| 2018/0008268 A1 | 1/2018 | Khairkhahan |
| 2018/0028215 A1 | 2/2018 | Cohen |
| 2018/0092661 A1 | 4/2018 | Prabhu |
| 2018/0133010 A1 | 5/2018 | Kizuka |
| 2018/0161159 A1 | 6/2018 | Lee |
| 2018/0360457 A1 | 12/2018 | Ellis et al. |
| 2019/0029790 A1 | 1/2019 | Bak-Boychuk et al. |
| 2019/0183571 A1 | 6/2019 | De Marchena |
| 2019/0298517 A1 | 10/2019 | Sanchez et al. |
| 2019/0307458 A1 | 10/2019 | Mathis et al. |
| 2020/0121460 A1 | 4/2020 | Dale et al. |
| 2021/0113232 A1 | 4/2021 | Ortiz et al. |
| 2021/0145574 A1 | 5/2021 | Childs et al. |

FOREIGN PATENT DOCUMENTS

| | | |
|---|---|---|
| CN | 103841899 | 6/2014 |
| CN | 104244841 A | 12/2014 |
| DE | 3504292 | 7/1986 |
| DE | 9100873 U1 | 4/1991 |
| DE | 10116168 | 11/2001 |
| EP | 0179562 | 7/1989 |
| EP | 0558031 | 2/1993 |
| EP | 0684012 | 11/1995 |
| EP | 0727239 | 8/1996 |
| EP | 0782836 | 7/1997 |
| EP | 1230899 A1 | 8/2002 |
| EP | 1674040 | 6/2006 |
| EP | 1980288 | 10/2008 |
| EP | 2005912 | 12/2008 |
| EP | 2537487 | 12/2012 |
| EP | 2641570 | 9/2013 |
| EP | 2702965 | 3/2014 |
| EP | 2740419 A1 | 6/2014 |
| EP | 3009103 | 4/2016 |
| FR | 2705556 | 12/1994 |
| FR | 2768324 | 3/1999 |
| FR | 2903292 A1 | 1/2008 |

(56) References Cited

FOREIGN PATENT DOCUMENTS

| | | |
|---|---|---|
| GB | 1598111 | 9/1981 |
| GB | 2151142 | 7/1985 |
| JP | 09-253030 A | 9/1997 |
| JP | 11-089937 A | 4/1999 |
| JP | 2000-283130 A | 10/2000 |
| JP | 2001-517529 A | 10/2001 |
| JP | 2006528911 | 12/2006 |
| JP | 2013516244 | 5/2013 |
| JP | 2013-523384 A | 6/2013 |
| JP | 2014523274 | 9/2014 |
| JP | 2015502548 | 1/2015 |
| JP | 2018-030008 A | 3/2018 |
| WO | WO 1981000668 | 3/1981 |
| WO | WO 1991001689 | 2/1991 |
| WO | 91/18881 A1 | 12/1991 |
| WO | 92/12690 A1 | 8/1992 |
| WO | WO 1994018881 | 9/1994 |
| WO | WO 1994018893 | 9/1994 |
| WO | WO 1995008292 | 3/1995 |
| WO | WO 1995011620 | 5/1995 |
| WO | WO 1995015715 | 6/1995 |
| WO | 96/14032 A1 | 5/1996 |
| WO | WO 1996020655 | 7/1996 |
| WO | WO 1996022735 | 8/1996 |
| WO | WO 1996030072 | 10/1996 |
| WO | WO 1997018746 | 5/1997 |
| WO | WO 1997025927 | 7/1997 |
| WO | WO 1997026034 | 7/1997 |
| WO | WO 1997038748 | 10/1997 |
| WO | WO 1997039688 | 10/1997 |
| WO | WO 1997048436 | 12/1997 |
| WO | WO 1998007375 | 2/1998 |
| WO | WO 1998024372 | 6/1998 |
| WO | WO 1998030153 | 7/1998 |
| WO | WO 1998032382 | 7/1998 |
| WO | WO 1998035638 | 8/1998 |
| WO | WO 1999000059 | 1/1999 |
| WO | WO 1999001377 | 1/1999 |
| WO | 99/07354 A2 | 2/1999 |
| WO | WO 1999007295 | 2/1999 |
| WO | WO 1999013777 | 3/1999 |
| WO | WO 1999044524 | 9/1999 |
| WO | 99/66967 A1 | 12/1999 |
| WO | 00/02489 A1 | 1/2000 |
| WO | WO 2000003651 | 1/2000 |
| WO | WO 2000003759 | 1/2000 |
| WO | WO 2000012168 | 3/2000 |
| WO | WO 2000044313 | 8/2000 |
| WO | 00/59382 A1 | 10/2000 |
| WO | WO 2000060995 | 10/2000 |
| WO | 01/00111 A1 | 1/2001 |
| WO | 01/03651 A2 | 1/2001 |
| WO | WO 2001000114 | 1/2001 |
| WO | 01/26586 A1 | 4/2001 |
| WO | 01/26587 A1 | 4/2001 |
| WO | 01/26588 A2 | 4/2001 |
| WO | 01/26703 A1 | 4/2001 |
| WO | WO 2001026557 | 4/2001 |
| WO | WO 2001028432 | 4/2001 |
| WO | WO 2001028455 | 4/2001 |
| WO | WO 2001047438 | 7/2001 |
| WO | WO 2001049213 | 7/2001 |
| WO | WO 2001050985 | 7/2001 |
| WO | 01/56721 A1 | 8/2001 |
| WO | WO 2001054618 | 8/2001 |
| WO | WO 2001066001 | 9/2001 |
| WO | WO 2001070320 | 9/2001 |
| WO | WO 2001089440 | 11/2001 |
| WO | 01/95831 A2 | 12/2001 |
| WO | 01/95832 A2 | 12/2001 |
| WO | 01/97741 A2 | 12/2001 |
| WO | WO 2002000099 | 1/2002 |
| WO | WO 2002001999 | 1/2002 |
| WO | WO 2002003892 | 1/2002 |
| WO | WO 2002034167 | 5/2002 |
| WO | 02/62270 | 8/2002 |
| WO | 02/62408 | 8/2002 |
| WO | WO 2002060352 | 8/2002 |
| WO | WO 2002062263 | 8/2002 |
| WO | WO 2003001893 | 1/2003 |
| WO | WO 2003003930 | 1/2003 |
| WO | WO 2003020179 | 3/2003 |
| WO | WO 2003028558 | 4/2003 |
| WO | WO 2003037171 | 5/2003 |
| WO | WO 2003047467 | 6/2003 |
| WO | WO 2003049619 | 6/2003 |
| WO | WO 2003073910 | 9/2003 |
| WO | WO 2003073913 | 9/2003 |
| WO | 03/82129 | 10/2003 |
| WO | WO 2003105667 | 12/2003 |
| WO | 2004/004607 A1 | 1/2004 |
| WO | WO 2004006810 | 1/2004 |
| WO | WO 2004012583 | 2/2004 |
| WO | WO 2004012789 | 2/2004 |
| WO | WO 2004014282 | 2/2004 |
| WO | WO 2004019811 | 3/2004 |
| WO | WO 2004030570 | 4/2004 |
| WO | WO 2004037317 | 5/2004 |
| WO | 2004/047679 A1 | 6/2004 |
| WO | WO 2004045370 | 6/2004 |
| WO | WO 2004045378 | 6/2004 |
| WO | WO 2004045463 | 6/2004 |
| WO | WO 2004062725 | 7/2004 |
| WO | WO 2004082523 | 9/2004 |
| WO | WO 2004082538 | 9/2004 |
| WO | 2004/093730 A2 | 11/2004 |
| WO | 2004/112651 A2 | 12/2004 |
| WO | WO 2004103162 | 12/2004 |
| WO | WO 2004112585 | 12/2004 |
| WO | 2005/002424 A2 | 1/2005 |
| WO | 2005/027797 A1 | 3/2005 |
| WO | WO 2005018507 | 3/2005 |
| WO | WO 2005032421 | 4/2005 |
| WO | WO 2005062931 | 7/2005 |
| WO | WO 2005112792 | 12/2005 |
| WO | WO 2006037073 | 4/2006 |
| WO | WO 2006105008 | 10/2006 |
| WO | WO 2006105009 | 10/2006 |
| WO | WO 2006113906 | 10/2006 |
| WO | 2006/115875 A2 | 11/2006 |
| WO | WO 2006115876 | 11/2006 |
| WO | WO 2007136829 | 11/2007 |
| WO | WO 2008103722 | 8/2008 |
| WO | WO 2010024801 | 3/2010 |
| WO | WO 2010121076 | 10/2010 |
| WO | WO 2012020521 | 2/2012 |
| WO | WO 2013049734 | 4/2013 |
| WO | WO 2013103934 | 7/2013 |
| WO | WO 2014064694 | 5/2014 |
| WO | WO 2014121280 | 8/2014 |
| WO | WO 2016022797 | 2/2016 |
| WO | WO 2016144708 | 9/2016 |
| WO | WO 2016150806 | 9/2016 |
| WO | WO 2017223073 | 12/2017 |
| WO | WO 2018009718 | 1/2018 |
| WO | WO 2018106482 | 6/2018 |
| WO | 2018/236766 A1 | 12/2018 |
| WO | 2019/040943 A1 | 2/2019 |
| WO | 2019/195336 A1 | 10/2019 |

OTHER PUBLICATIONS

Abe et al, "De Vega's Annuloplasty for Acquired Tricuspid Disease: Early and Late Results in 110 Patients", Ann. Thorac. Surg., pp. 670-676, vol. 48 (Jan. 1989).

Abe et al., "Updated in 1996—De Vega's Annuloplasty for Acquired Tricuspid Disease: Early and Late Results in 110 Patients", Ann. Thorac. Surg., pp. 1876-1877, vol. 62 (1996).

Alfieri et al., "An Effective Technique to Correct Anterior Mitral Leaflet Prolapse," J. Card Surg., 14:468-470 (1999).

Alfieri et al., "Novel Suture Device for Beating Heart Mitral Leaflet Approximation," Annals of Thoracic Surgery, 74:1488-1493 (2002).

(56) References Cited

OTHER PUBLICATIONS

Alfieri et al., "The double orifice technique in mitral valve repair: a simple solution for complex problems," Journal of Thoracic and Cardiovascular Surgery, 122:674-681 (2001).
Alfieri et al., "The edge to edge technique," The European Association for Cardio-Thoracic Surgery 14th Annual Meeting, Oct. 7-11, 2000, Book of Proceedings.
Ali Khan et al, Blade Atrial Septostomy: Experience with the First 50 Procedures, Cathet. Cardiovasc. Diagn., Aug. 1991, pp. 257-262, vol. 23.
Alvarez et al, Repairing the Degenerative Mitral Valve: Ten to Fifteen-year Follow-up, Journal of Thoracic Cardiovascular Surgery, Aug. 1996, pp. 238-247, vol. 112, No. 2.
Bailey, "Mitral Regurgitation" in Surgery of the Heart, Chapter 20, pp. 686-737 (1955).
Borghetti et al., "Preliminary observations on haemodynamics during physiological stress conditions following 'double-orifice' mitral valve repair," European Journal of Cardio-thoracic Surgery, 20:262-269 (2001).
Castedo, "Edge-to-Edge Tricuspid Repair for Redeveloped Valve Incompetence after DeVega's Annuloplasty," Ann Thora Surg., 75:605-606 (2003).
Chinese Office Action issued in Chinese Application No. 200980158707.2 dated Sep. 9, 2013.
Communication dated Apr. 16, 2018 from the European Patent Office in counterpart European application No. 04752603.3.
Communication dated Apr. 28, 2017 issued by the European Patent Office in counterpart application No. 16196023.2.
Communication dated Jan. 26, 2017, from the European Patent Office in counterpart European application No. 16196023.2.
Dang N C et al., "Surgical Revision After Percutaneous Mitral Valve Repair with a Clip: Initial Multicenter Experience",The Annals of Thracic Surgery,Elsevier, United States, vol. 80, No. 6, pp. 2338-2342, (Dec. 1, 2005), XP027732951, ISSN:0003-4975 [retrieved on Dec. 1, 2005].
Dottori et al., "Echocardiographic imaging of the Alfieri type mitral valve repair," Ital. Heart J., 2(4):319-320 (2001).
Downing et al., "Beating heart mitral valve surgery: Preliminary model and methodology," Journal of Thoracic and Cardiovascular Surgery, 123(6):1141-1146 (2002).
Extended European Search Report, dated Oct. 17, 2014, issued in European Patent Application No. 06751584.1.
Falk et al., "Computer-Enhanced Mitral Valve Surgery: Toward a Total Endoscopic Procedure," Seminars in Thoracic and Cardiovascular Surgery, 11(3):244-249 (1999).
Feldman et al, Randomized Comparison of Percutaneous Repair and Surgery for Mitral Regurgitation: 5-Year Results of Everest II. J Am Coll Cardiol. Dec. 29, 2015; 66(25):2844-2854.
Fucci et al, Improved Results with Mitral Valve Repair Using New Surgical Techniques, Eur. J. Cardiothorac. Surg., Nov. 1995, pp. 621-627, vol. 9.
Garcia-Rinaldi et al., "Left Ventricular Volume Reduction and Reconstruction is Ischemic Cardiomyopathy," Journal of Cardiac Surgery, 14:199-210 (1999).
Izzat et al., "Early Experience with Partial Left Ventriculectomy in the Asia-Pacific Region," Annuals of Thoracic Surgery, 67:1703-1707 (1999).
Kallner et al., "Transaortic Approach for the Alfieri Stitch," Ann Thorac Surg, 71:378-380 (2001).
Kavarana et al., "Transaortic Repair of Mitral Regurgitation," The Heart Surgery Forum, #2000-2389, 3(1):24-28 (2000).
Khan et al., "Blade Atrial Septostomy; Experience with the First 50 Procedures", Catheterization and Cardiovascular Diagnosis, 23:257-262 (1991).
Kron et al., "Surgical Relocation of the Posterior Papillary Muscle in Chronic Ischemic Mitral Regurgitation," Annals. Of Thoracic Surgery, 74:600-601 (2002).
Kruger et al., "P73—Edge to Edge Technique in Complex Mitral Valve Repair," Thorac Cardiovasc Surg., 48(Suppl. 1):106 (2000).

Maisano et al., "Valve Repair for Traumatic Tricuspid Regurgitation," Eur. J. Cardio-Thorac Surg, 10:867-873 (1996).
Maisano et al., "The Edge-to-edge Technique: A Simplified Method to Correct Mitral Insufficiency", Eur. J. Cardiothorac. Surg., pp. 240-246, vol. 13 (Jan. 14, 1998).
Maisano et al., "The Double Orifice Repair for Barlow Disease: a Simple Solution for a Complex Repair," Supplement I Circulation, 100(18):1-94 (Nov. 1999).
Maisano et al., "The Hemodynamic Effects of Double-Orifice Valve Repair for Mitral Regurgitation: a 3D Computational Model," European Journal of Cardio-thoracic Surgery, 15:419-425 (1999).
Maisano et al., "The Double Orifice Technique as a Standardized Approach to Treat Mitral Regurgitation due to Severe Myxomatous Disease: Surgical Technique," European Journal of Cardio-thoracic Surgery, 17:201-205 (2000).
Maisano et al., "The Future of Transcatheter Mitral Valve Interventions: Competitive or Complementary Role of Repair vs. Replacement?", Eur Heart J.36(26):1651-1659 ( Jul. 7, 2015 ).
Mantovani et al., "Edge-to-edge Repair of Congenital Familiar Tricuspid Regurgitation: Case Report," J. Heart Valve Dis., 9:641-643 (2000).
McCarthy et al, "Tricuspid Valve Repair With the Cosgrove-Edwards Annuloplasty System", Ann. Thorac. Surg., 64:267-8 ( Jan. 16, 1997).
McCarthy et al., "Partial Left Ventriculectomy and Mitral Valve Repair for End-Stage Congestive Heart Failure," European Journal of Cardio-thoracic Surgery, 13:337-343 (1998).
Moainie et al., "Correction of Traumatic Tricuspid Regurgitation Using the Double Orifice Technique," Annals of Thoracic Surgery, 73:963-965 (2002).
Morales et al., "Development of an Off Bypass Mitral Valve Repair," The Heart Surgery Forum #1999-4693, 2(2):115-120 (1999).
Nakanishi et al., "Early Outcome with the Alfieri Mitral Valve Repair," J. Cardiol., 37: 263-266 (2001) [Abstract in English; Article in Japanese].
Nielsen et al., "Edge-to-Edge Mitral Repair: Tension of the Approximating Suture and Leaflet Deformation During Acute Ischemic Mitral Regurgitation in the Ovine Heart," Circulation, 104(Suppl. I):I-29-I-35 (2001).
Nishimura et al, 2014 AHA/ACC guideline for the management of patients with valvular heart disease: executive summary: a report of the American College of Cardiology/American Heart Association Task Force on Practice Guidelines. J Am Coll Cardiol. Jun. 10, 2014; 63(22):2438-2488.
Osawa et al., "Partial Left Ventriculectomy in a 3-Year Old Boy with Dilated Cardiomyopathy," Japanese Journal of Thoracic and Cardiovascular Surg, 48:590-593 (2000).
Park et al., Clinical Use of Blade Atrial Septostomy, Circulation, pp. 600-608, vol. 58, No. 4 (1978 ).
Patel et al., #57 Epicardial Atrial Defibrillation: Novel Treatment of Postoperative Atrial Fibrillation, 2003 STS Presentation, [Abstract Only].
Privitera et al., "Alfieri Mitral Valve Repair: Clinical Outcome and Pathology," Circulation, 106:e173-e174 (2002).
Redaelli et al., "A Computational Study of the Hemodynamics After 'Edge-To-Edge' Mitral Valve Repair," Journal of Biomechanical Engineering, 123:565-570 (2001).
Reul et al., "Mitral Valve Reconstruction for Mitral Insufficiency," Progress in Cardiovascular Diseases, XXXIX(6):567-599 (1997).
Rose et al., "Late MitraClip Failure: Removal Technique for Leaflet-Sparing Mitral Valve Repair", Journal of Cardiac Surgery, (Jul 4, 2012), XP055047339, DOI: 10.1111/j. 1540-8191.2012.01483.x [retrieved on Nov. 11, 2012].
Takizawa H et al: "Development of a microfine active bending catheter equipped with MIF tactile sensors", Micro Electro Mechanical Systems, 1999. MEMS '99. Twelfth IEEE Interna T i0nal Conference on Orlando, FL, USA Jan. 17-21, 1999, Piscataway, NJ, USA,IEEE, US, Jan. 17, 1999 (Jan. 17, 1999), pp. 412-417, XP010321677, ISBN: 978-0-7803-5194-3 figures 1-3.
Tamura et al., "Edge to Edge Repair for Mitral Regurgitation in a Patient with Chronic Hemodialysis: Report of A Case," Kyobu Geka. The Japanese Journal of Thoracic Surgery, 54(9):788-790 (2001).

(56) References Cited

OTHER PUBLICATIONS

Timek et al., "Edge-to-edge mitral repair: gradients and three-dimensional annular dynamics in vivo during inotropic stimulation," Eur J. of Cardiothoracic Surg., 19:431-437 (2001).
Totaro, "Mitral valve repair for isolated prolapse of the anterior leaflet: an 11-year follow-up," European Journal of Cardio-thoracic Surgery, 15:119-126 (1999).
Uchida et al., Percutaneous Cardiomyotomy and Valvulotomy with Angioscopic Guidance, Am. Heart J., pp. 1221-1224, vol. 121 (Apr. 1991).
Umana et al., 'Bow-Tie' Mitral Valve Repair: An Adjuvant Technique for Ischemic Mitral Regurgitation, Ann. Thorac. Surg., pp. 1640-1646, vol. 66 (May 12, 1998).
Votta et al., "3-D Computational Analysis of the Stress Distribution on the Leaflets after Edge-to-Edge Repair of Mitral Regurgitation," Journal of Heart Valve Disease, 11:810-822 (2002).
U.S. Appl. No. 14/216,787, Apr. 8, 2016, Office Action.
U.S. Appl. No. 14/216,787, Nov. 7, 2016, Notice of Allowance.
U.S. Appl. No. 14/216,813, Mar. 9, 2017, Office Action.
U.S. Appl. No. 14/216,813, Dec. 15, 2017, Office Action.
U.S. Appl. No. 14/216,813, Apr. 6, 2018, Office Action.
U.S. Appl. No. 14/577,852, Oct. 20, 2016, Office Action.
U.S. Appl. No. 14/577,852, May 16, 2017, Office Action.
U.S. Appl. No. 14/577,852, Sep. 7, 2017, Office Action.
U.S. Appl. No. 14/577,852, Apr. 25, 2018, Notice of Allowance.
U.S. Appl. No. 15/423,060, Apr. 25, 2019, Office Action.
U.S. Appl. No. 15/423,060, Aug. 19, 2019, Office Action.
U.S. Appl. No. 15/423,060, Oct. 28, 2019, Office Action.
U.S. Appl. No. 15/423,060, Jan. 27, 2020, Notice of Allowance.
U.S. Appl. No. 15/642,245, Aug. 9, 2019, Office Action.
U.S. Appl. No. 15/642,245, Nov. 6, 2019, Notice of Allowance.
U.S. Appl. No. 15/642,245, Jan. 29, 2020, Notice of Allowance.
U.S. Appl. No. 15/642,245, Mar. 27, 2020, Notice of Allowance.
U.S. Appl. No. 15/724,545, Dec. 27, 2019, Office Action.
U.S. Appl. No. 15/724,545, May 1, 2020, Office Action.
Agricola et al., "Mitral Valve Reserve in Double Orifice Technique: an Exercise Echocardiographic Study," Journal of Heart Valve Disease, 11(5):637-643 (2002).
Alfieri, "The Edge-to-Edge Repair of the Mitral Valve," [Abstract] 6th Annual New Era Cardiac Care: Innovation & Technology, Heart Surgery Forum, (Jan. 2003) pp. 103.
Arisi et al., "Mitral Valve Repair with Alfieri Technique in Mitral Regurgitation of Diverse Etiology: Early Echocardiographic Results," Circulation Supplement II, 104(17):3240 (2001).
Bach et al, Early Improvement in Congestive Heart Failure After Correction of Secondary Mitral Regurgitation in End-stage Cardiomyopathy, American Heart Journal, Jun. 1995, pp. 1165-1170, vol. 129, No. 6.
Bach et al., Improvement Following Correction of Secondary Mitral Regurgitation in End-stage Cardiomyopathy With Mitral Annuloplasty, Am. J. Cardiol., Oct. 15, 1996, pp. 966-969, vol. 78.
Bernal et al., "The Valve Racket: a new and different concept of atrioventricular valve repair," Eur. J. Cardio-thoracic Surgery 29:1026-1029 (2006).
Bhudia et al., "Edge-to-Edge (Alfieri) Mitral Repair: Results in Diverse Clinical Settings," Ann Thorac Surg, 77:1598-1606 (2004).
Bhudia, #58 Edge-to-edge mitral repair: a versatile mitral repair technique, 2003 STS Presentation, [Abstract Only], 2004.
Bolling et al., Surgery for Acquired Heart Disease: Early Outcome of Mitral Valve Reconstruction in Patients with End-stage Cardiomyopathy, Journal of Thoracic and Cariovascular Surgery, Apr. 1995, pp. 676-683, vol. 109, No. 4.
Communication dated May 8, 2017, from the European Patent Office in counterpart European Application No. 04752714.8.
Dec et al, Idiopathic Dilated Cardiomyopathy, The New England Journal of Medicine, Dec. 8, 1994, pp. 1564-1575, vol. 331, No. 23.
Filsoufi et al., "Restoring Optimal Surface of Coaptation With a Mini Leaflet Prosthesis: A New Surgical Concept for the Correction of Mitral Valve Prolapse," Intl. Soc. for Minimally Invasive Cardiothoracic Surgery 1(4):186-87 (2006).

Frazier et al., #62 Early Clinical Experience with an Implantable, Intracardiac Circulatory Support Device: Operative Considerations and Physiologic Implications, 2003 STS Presentation, 1 page total. [Abstract Only].
Fundaro et al., "Chordal Plication and Free Edge Remodeling for Mitral Anterior Leaflet Prolapse Repair: 8-Year Follow-up," Annals of Thoracic Surgery, 72:1515-1519 (2001).
Gateliene, "Early and postoperative results results of metal and tricuspid valve insufficiency surgical treatment using edge-to-edge central coaptation procedure," (Oct. 2002) 38 (Suppl 2):172 175.
Gatti et al., "The edge to edge technique as a trick to rescue an imperfect mitral valve repair," Eur. J. Cardiothorac Surg, 22:817-820 (2002).
Gundry, "Facile mitral valve repair utilizing leaflet edge approximation: midterm results of the Alfieri figure of eight repair," Presented at the Meeting of the Western Thoracic Surgical Association, (1999).
Gupta et al., #61 Influence of Older Donor Grafts on Heart Transplant Survival: Lack of Recipient Effects, 2003 STS Presentation, [Abstract Only].
Ikeda et al., "Batista's Operation with Coronary Artery Bypass Grafting and Mitral Valve Plasty for Ischemic Dilated Cardiomyopathy," The Japanese Journal of Thoracic and Cardiovascular Surgery, 48:746-749 (2000).
International Search Report and Written Opinion dated Sep. 11, 2017 for International PCT Patent Application No. PCT/US2017/040977.
International Search Report and Written Opinion of PCT Application No. PCT/US2009/068023, dated Mar. 2, 2010, 10 pages total.
Kameda et al., Annuloplasty for Severe Mitral Regurgitation Due to Dilated Cardiomyopathy, Ann. Thorac. Surg., 1996, pp. 1829-1832, vol. 61.
Kaza et al., "Ventricular Reconstruction Results in Improved Left Ventricular Function and Amelioration of Mitral Insufficiency," Annals of Surgery, 235(6):828-832 (2002).
Kherani et al., "The Edge-To-Edge Mitral Valve Repair: The Columbia Presbyterian Experience," Ann. Thorac. Surg., 78:73-76 (2004).
Langer et al., "Posterior mitral leaflet extensions: An adjunctive repair option for ischemic mitral regurgitation?" J Thorac Cardiovasc Surg, 131:868-877 (2006).
Lorusso et al., "The double-orifice technique for mitral valve reconstruction: predictors of postoperative outcome," Eur J. Cardiothorac Surg, 20:583-589 (2001).
McCarthy et al., "Tricuspid Valve Repair With the Cosgrove-Edwards Annuloplasty System", Ann. Throac Surg. 64:267-8 (Jan. 16, 1997).
Noera et al., "Tricuspid Valve Incompetence Caused by Nonpenetrating Thoracic Trauma", Annals of Thoracic Surgery, 51:320-322 (1991).
Ricchi et al., Linear Segmental Annuloplasty for Mitral Valve Repair, Ann. Thorac. Surg., Jan. 7, 1997, pp. 1805-1806, vol. 63.
Robicsek et al., #60 The Bicuspid Aortic Valve: How Does It Function? Why Does It Fail? 2003 STS Presentation, [Abstract Only].
Supplemental European Search Report of EP Application No. 02746781, dated May 13, 2008, 3 pages total.
Supplementary European Search Report issued in European Application No. 05753261.6 dated Jun. 9, 2011, 3 pages total.
Tager et al, Long-Term Follow-Up of Rheumatic Patients Undergoing Left-Sided Valve Replacement With Tricuspid Annuloplasty—Validity of Preoperative Echocardiographic Criteria in the Decision to Perform Tricuspid Annuloplasty, Am. J. Cardiol., Apr. 15, 1998, pp. 1013-1016, vol. 81.
Tibayan et al., #59 Annular Geometric Remodeling in Chronic Ischemic Mitral Regurgitation, 2003 STS Presentation, [Abstract Only].
Timek, "Edge-to-Edge Mitral Valve Repair without Annuloplasty Ring in Acute Ischemic Mitral Regurgitation," [Abstract] Clinical Science, Abstracts from Scientific Sessions, 106(19):2281 (2002).
U.S. Provisional Application Filed on Jul. 6, 2016, by Khairkhahan., U.S. Appl. No. 62/359,121.

(56) References Cited

OTHER PUBLICATIONS

U.S. Provisional Application Filed on Nov. 7, 2016, by Khairkhahan., U.S. Appl. No. 62/418,571.
U.S. Provisional Application Filed on Oct. 22, 2018, by Dale et al., U.S. Appl. No. 62/748,947.
Umana et al., "'Bow-tie' Mitral Valve Repair Successfully Addresses Subvalvular Dysfunction in Ischemic Mitral Regurgitation," Surgical Forum, XLVIII:279-280 (1997).
U.S. Appl. No. 14/216,813, filed Mar. 17, 2014, Hernandez.

* cited by examiner

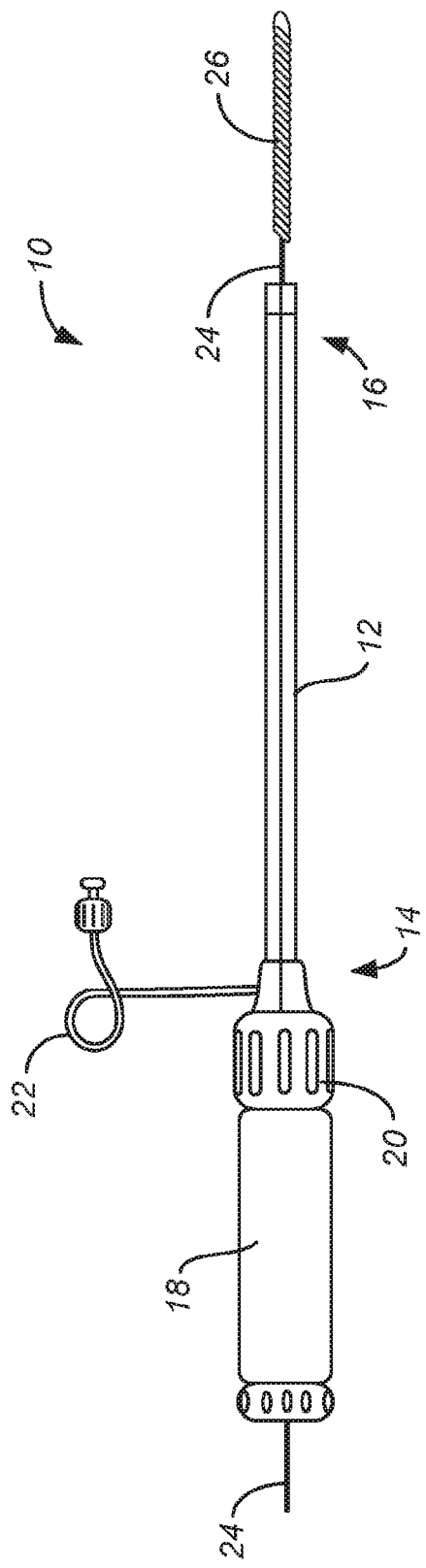
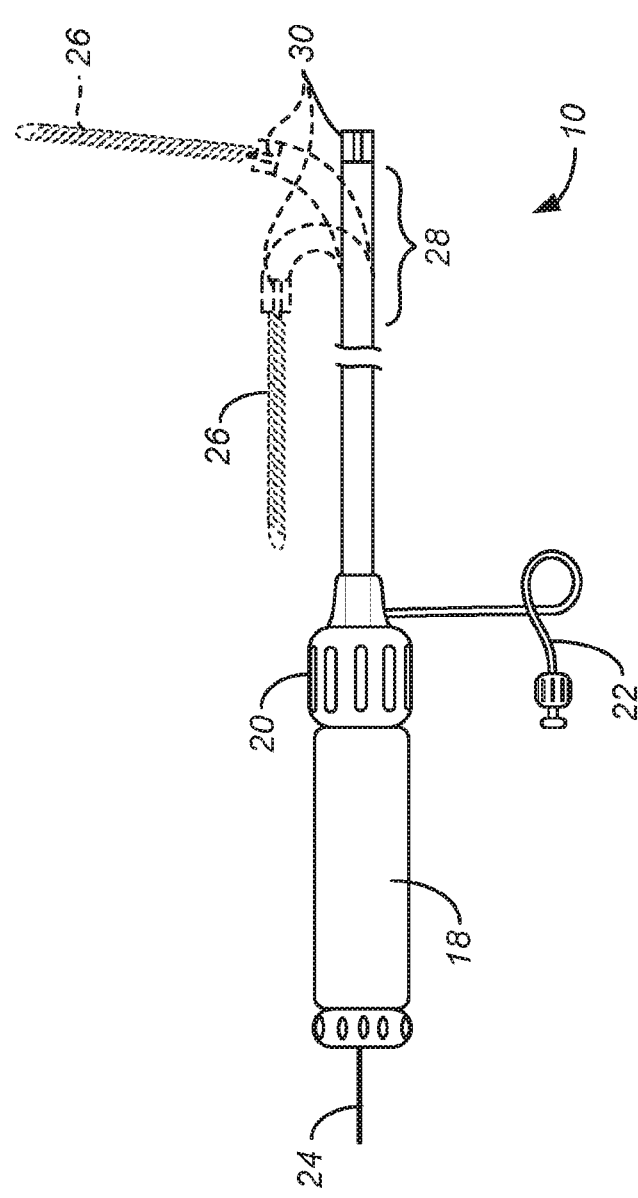
FIG. 2A
FIG. 2B

METHODS AND DEVICES FOR VALVE CLIP EXCISION

CROSS-REFERENCE TO RELATED APPLICATION THE INVENTION

The present application is a divisional application of U.S. patent application Ser. No. 15/642,245, filed Jul. 5, 2017, now U.S. Pat. No. 10,736,632, which claims the benefit of provisional application No. 62/359,121, filed on Jul. 6, 2016, and of provisional application No. 62/418,571, filed on Nov. 7, 2016, the full disclosures of which are incorporated herein by reference.

BACKGROUND OF THE INVENTION

1. The Field of the Invention

The prevent invention relates generally to medical devices and methods. More particularly, the present invention relates to devices, systems, kits, and methods for removing clips and other implanted prostheses from heart valves.

Mitral regurgitation is a commonly encountered valvular disorder and prevalence increases with age. In this condition, blood regurgitates abnormally from the left ventricle into the left atrium during cardiac systole, and this condition can result in numerous adverse consequences such as heart failure due to left ventricular dysfunction, atrial fibrillation, pulmonary hypertension, and death. Published guidelines recommend surgical or transcatheter correction of mitral regurgitation to improve the clinical condition.

Transcatheter correction of mitral regurgitation by implantation of a mitral valve clip (in particular the Mitra-Clip® system from Abbott Vascular) has become a standard therapy for patients at high risk for open surgical corrective procedures. Such clip implantation procedures are performed through a guiding catheter that is inserted into the right femoral vein. One or more mitral valve clips can be delivered through the guiding catheter and implanted to re-approximate the anterior and posterior mitral leaflets (often referred to as an "edge-to-edge" repair). The Mitra-Clip® mitral valve clip is metallic implant made of a cobalt chromium alloy and covered with a fabric mesh.

To date, over 45,000 procedures using the MitraClip® valve clip have been performed globally and there are currently nearly 1000 procedures performed each month. The MitraClip® procedure has been found to be very safe procedure and provides a therapeutic option for patients at high surgical risk.

There are, however, some significant limitations to conventional mitral valve clip technology. First, once a mitral valve clip is implanted, removal typically requires open surgical excision. Second, not all patients achieve satisfactory MR reduction at the time of the procedure due to technical challenges. Finally, up to 1 in 5 patients may have return of significant MR or have need for a repeat intervention within 6 months of the MitraClip® procedure.

If patients have recurrent MR after a mitral valve clip procedure, current options for additional treatment are limited. One option would be to place another mitral valve clip but this is often not possible due to concern for creating mitral stenosis (a mitral valve clip often narrows the valve so that the valve no longer opens properly).

Other options include a variety of mitral valve repair and replacement technologies which are becoming available. Of great interest are transcatheter mitral valve replacement procedures where a bio-prosthetic mitral valve mounted on an expandable frame is deployed in a defective native mitral valve. Such transcatheter "replacement" valves offer complete elimination of mitral regurgitation and would mimic the surgical "gold standard" of mitral valve replacement in selected patients.

At the present time, it can be difficult or impossible to implant a transcatheter mitral valve when a prior mitral valve clip procedure has been performed, since the mitral valve clip(s) interfere and will not allow complete expansion of the new valve. It would therefore be desirable to provide devices, systems, kits, and methods for the transcatheter removal of clips and other implanted prostheses from heart valves. It would be particularly desirable that such devices, systems, kits, and methods for the transcatheter removal of clips and other implanted prostheses from heart valves would leave the heart valve in condition to receive a subsequent transcatheter procedure, such as prosthetic valve implantation, to treat the valve pathology. At least some of these objectives will be met by the inventions described herein.

2. Description of the Background Art

See US Patent Publs. 2014/0228871; US2015257883; and US2014135799; U.S. Pat. Nos. 8,500,768; 7,955,340; and 5,895,404; as well as the following guidelines and publications: Nishimura R A, Otto C M, Bonow R O et al. 2014 AHA/ACC guideline for the management of patients with valvular heart disease: executive summary: a report of the American College of Cardiology/American Heart Association Task Force on Practice Guidelines. J Am Coll Cardiol 2014; 63:2438-88; Feldman T, Kar S, Elmariah S et al. Randomized Comparison of Percutaneous Repair and Surgery for Mitral Regurgitation: 5-Year Results of EVEREST II. J Am Coll Cardiol 2015; 66:2844-54; and Maisano F, Alfieri O, Banai S et al. The future of transcatheter mitral valve interventions: Competitive or complementary role of repair vs. replacement?, Eur Heart J 2015; 36:1651-9.

SUMMARY OF THE INVENTION

The present invention provides transcatheter tools and procedures that can be used to separate and optionally remove one or more mitral valve clips from native mitral leaflet tissue. In such procedures, the physician can insert specifically designed catheters either from the left atrium or left ventricle. A guidewire may be placed around the leaflet and valvular tissue adjacent to the previously implanted mitral valve clip. Utilizing mechanical cutting or abrasion, or radiofrequency energy, the mitral valve clips may be excised from either the anterior or posterior leaflets, or both, restoring the native valve orifice and allowing future repair or replacement therapy. After separation of the mitral valve clips from native leaflet tissue, the degree of mitral regurgitation would be expected to worsen acutely. The separation procedure of the present invention in contrast can be performed immediately prior to transcatheter valve implantation or another transcatheter corrective procedure. For instance, if transapical access were used for deployment of a new transcatheter mitral valve, then transseptal access could be used to release the mitral valve clips, or vice versa.

In a first aspect of the present invention, a method for excising a clip approximating an opposed pair of valve leaflets in a heart valve comprises introducing a capture catheter into a heart chamber adjacent to the valve leaflets on one side of the clip. A transfer catheter is also introduced into the heart chamber adjacent to the valve leaflets on another side of the clip, and a cutting member is deployed between the transfer catheter and the capture catheter to place or engage the cutting member against tissue of at least one of the valve leaflets. The cutting number is then used to excise the clip from at least one of the valve leaflets to release fixation and allow separation of the valve leaflets.

The excision methods of the present invention are useful on any heart valve where a clip may have been placed to enhance coaptation or for other reasons. Most typically, the heart valve is a mitral valve, and the catheters may be introduced transseptally into the left atrium above the valve or may introduced transapically into the left ventricle beneath the mitral valve. In other instances, the target heart valve can be a tricuspid valve, and the catheters may be introduced into the right atrium above the tricuspid valve or into the right ventricle below the tricuspid valve.

In exemplary embodiments, deploying the cutting member comprises steering a tip of at least one and usually both of the capture catheter and the transfer catheter to bring the tips of both catheters into proximity with the valve clip. Typically, at least one of the capture catheter and transfer catheter may be advanced through an opening between the valve leaflets adjacent to the fixed valve clip, where the advanced catheter may then be steered around the opposite side of the valve clip and brought up through the space between the valve leaflets on an opposite side of the valve clip. The cutting member may then be passed between the transfer catheter and the capture catheter to span a target region of the valve leaflet to be excised. The catheters may then be manipulated to extend the cutting member past a side of the valve clip so that the cutting member is positioned to excise a portion of the valve leaflet on one side of the valve. As will be described in more detail below, the valve clip may be left implanted in the opposed valve leaflet, and a subsequent valve intervention procedure performed with the clip left attached to the opposed valve leaflet. Alternatively, the capture and transfer catheters may be used to reposition the cutting member on the other side of the valve clip so that the opposed leaflet may be excised from the clip to completely release the clip and allow the clip to be removed from the heart prior to performing a subsequent intervention on the heart valve. When releasing and removing the valve clip, it will of course be necessary that the valve clip be constrained, typically by a removal catheter as described herein below.

In still further specific examples, the cutting member may be deployed by engaging a magnetic element on the capture catheter against a magnetic element on the cutting member. The magnetic elements are typically at the tip of the capture catheter and an end of the cutting member, and the catheter(s) may be manipulated to draw the cutting member past either or both sides of the valve clip in order to excise of the valve leaflet tissue to release the clip.

In an alternative embodiment, the cutting element may comprise a loop which is used to capture a free end of the cutting member, and the capture catheter may then be manipulated to advance the loop over a free end of the cutting member and draw the cutting member past the clip through the valve tissue.

In still further embodiments, deploying the cutting member may comprise drawing the tips of the capture catheter and the transfer catheter together to form a path past the valve clip and advancing the element over the path. After such advancement and positioning of the cutting member, the capture catheter and/or the transfer catheter may be manipulated to manipulate the cutting member to excise the valve tissue to release the clip.

As discussed above, in some embodiments of the methods of the present invention, the clip(s) will be excised from one valve leaflet only, leaving the clip(s) implanted in an opposed valve leaflet. Freeing of the clip(s) from at least one valve leaflet will in at least some cases be sufficient to release the opposed valve leaflets and enable performance of the subsequent valve replacement or other interventional procedure. In other instances, however, it will be preferable to completely remove the valve clip(s) from the heart valve prior to performing a subsequent valve implantation or other intervention. In such cases, a removal catheter or other device will typically be used to constrain or capture the clip(s) during the excision and withdraw the excised clip(s) from the heart chamber prior to any further intervention.

In still other specific embodiments of the methods of the present invention, the clip(s) may be excised from the valve leaflet tissue in a variety of ways. For example, the cutting member may comprise an electrode segment or other electrically conductive region capable of delivering a radiofrequency (RF) cutting current to the tissue. In particular, the RF current would be delivered in a cutting mode so that the cutting member could excise the valve tissue adjacent to the valve clip. In other instances, the cutting member could comprise a sharpened or abrasive region which could be used to mechanically cut through the valve tissue. For example, a sharpened or abrasive cutting region could be reciprocated so that it would "saw" through the tissue in order to excise the valve. Other known tissue cutting modalities could also be employed.

As described thus far, the capture catheter, transfer catheter, and cutting member are used to excise the tissue from a single valve leaflet, leaving the valve clip attached to the opposed valve leaflet. While removing the valve from a single leaflet will allow sufficient opening of the leaflets for subsequent prosthetic valve implantation or other corrective procedures, it will sometimes be desirable to remove the valve clip from both opposed valve leaflets. In such instances, it will be preferred to introduce a clip removal catheter into the heart chamber in order to stabilize the eventually remove the valve clip. A distal end of the clip removal catheter can be engaged against the clip and will usually be attached to the clip while the clip is excised from one or both valve leaflets using the cutting member.

In still further exemplary embodiments, the capture catheter, the transfer catheter, and optionally the clip removal catheter can be introduced transseptally, usually simultaneously through a transseptal catheter or sheath. In still other specific embodiments, the capture catheter, the transfer catheter, and optionally the clip removal catheter can be introduced transapically, typically simultaneously through a transapical sheath or catheter.

In a second aspect of the present invention, a system for excising an implanted clip approximating opposed valve leaflets in the heart valve comprises a capture catheter, a transfer catheter, and a cutting member. The capture catheter is configured to be introduced into a heart chamber adjacent to the valve leaflets on one side of the clip. The transfer catheter is configured to be introduced into the heart chamber adjacent to the valve leaflets on another side of the clip, and the cutting member is configured to be deployed from the transfer catheter to the capture catheter to place the cutting element against tissue of at least one of the valve leaflets to excise the clip.

In specific aspects of the system, at least one of the capture catheter and the transfer catheter will have a steerable tip, usually both having a steerable tip. The capture catheter will often have a magnetic distal tip configured to engage and capture a magnetic element disposed at the distal end of the cutting member. In this way, the magnetic tip on the capture catheter can be used to attract and engage the magnetic end of the cutting member so that the cutting member can be deployed between the capture catheter and the transfer catheter. Thus, a cutting region of the cutting member can be positioned to engage the valve leaflet tissue adjacent to the valve clip so that the cutting region can be used to cut the tissue and excise the clip. For example, the cutting region could comprise a sharpened or abrasive region which can be used to mechanically cut the valve tissue. Alternatively, the cutting region could comprise an RF electrode which can be powered with a cutting current to excise the valve leaflet tissue adjacent to the clip.

The systems of the present invention may further comprise an introductory sheath, typically a transseptal sheath or a transapical sheath, for delivering the catheters of the present invention to a heart chamber. Usually, the introductory sheath will be sufficiently large to accommodate at least the capture catheter and the transfer catheter simultaneously. Often times, the system will further comprise a removal catheter, and the introductory sheath will be sized to be sufficiently large to simultaneously accommodate each of the capture catheter, transfer catheter, and removal catheter.

The clip removal catheter of the present invention will typically have a distal end configured to engage and capture the clip Certain valve clips, such as the MitraClip® valve clip, have a unique shape that provides a "docking" feature which can be used by the clip removal and optionally other catheters of the present invention to "dock" with either the atrial or ventricular aspect of the valve clip. The shape of the valve clip(s) is typically easy to discern on fluoroscopy which facilitates targeting and optionally docking a removal or other catheter with the clip during a removal procedure. Such docking has several advantages. First, docking can stabilize the valve clip relative to the catheter system which is advantageous as the valves are moving during the beating heart procedure. Second, docking facilitates orienting the catheter(s) to improve position of the cutting member, e.g. looping a cutting wire so that it encircles the clip using either the magnetic or snare techniques shown above. Third, by docking a removal or other catheter with the valve clip, the catheter and cutting member can be stably positioned in close proximity to the valve clip, thus minimizing the risk of entangling or snaring the chordal apparatus with the loop wire or other cutting member. Fourth, docking can be performed either from an atrial or a ventricular aspect. For example, atrial docking can be achieved by docking into a groove on the top of a "Y" portion of the MitraClip® clip. Ventricular docking may be achieved by docking with the bottom of the "Y" portion of the MitraClip® clip. The docking can be passive, e.g. via an interference fit, or can be active where the removal or other catheter has a "grasping" feature to securely attach the MitraClip® clip. Docking can be performed on each valve clip individually or on several at the same time with modification in the docking feature.

The removal catheters of the present invention may be designed to dock with the MitraClip® or other valve clips to place a snare around the clip. After the clip is freed from both the anterior and posterior leaflets (or septal leaflet in case of a tricuspid valve) using the previously described catheters, the clip can be removed from the body through the access sheath by the removal catheter. The removal catheter may have any one of a variety of clip-grasping features, such as a snare, biopsy-type forceps, or jaws that secure the valve clip to hold it after it has been freed from both leaflets so it can be removed from the body. The capture and/or transfer catheter may also be configured to dock with the valve clip, e.g. have a distal tip with a shape complementary to the shape of the valve clip. The catheter that removes the clip can be placed via a transvenous transseptal approach or left ventricular transapical approach. In some instances, a removal catheter can be designed with a funnel shaped tip to allow the valve clip to be drawn into the catheter with proper orientation.

The catheter systems of the present invention can also be used to encircle and remove pacemaker or defibrillator leads. For example, by sliding a loop encircling the lead along a length of the lead, the lead can be excised from the heart or vascular tissue in which it has been implanted. In particular, the catheters of the present invention can be used to free leads from vascular venous tissue such as the axillary vein, brachiocephalic vein, and/or superior vena cava. The catheters of the present invention can also be used to free leads from a tricuspid valve or the right ventricular myocardium. In particular, a lead may be freed from the tricuspid valve in situations where the lead may be causing tricuspid regurgitation (TR). The lead could optionally be repositioned to reduce TR. The catheters can also be used to free a lead to allow the lead to be repositioned in the tricuspid valve orifice as desired to facilitate placement of a transcatheter valve in the tricuspid position.

The novel features believed characteristic of the illustrative examples are set forth in the appended claims. The illustrative examples, however, will best be understood by reference to the following detailed description of an illustrative example of the present disclosure when read in conjunction with the accompanying drawings, wherein:

BRIEF DESCRIPTION OF THE DRAWINGS

FIGS. 2A and 2B illustrate a capture catheter constructed in accordance with the principles of the present invention with a steerable distal region shown in its straightened configuration (FIG. 2A) and in deflected configurations (FIG. 2B).

DETAILED DESCRIPTION OF THE INVENTION

The present invention provides apparatus and methods for the separation of one or more valve clips from mitral and other heart valve leaflets. The valve clips can be located anywhere along the valve coaptation plane (central, medial, lateral, or commissural), and in some embodiments the valve clips are removed from one of the coapting valve leaflets while being left in placed in the other of the coapting valve leaflets. In other embodiments, the valve clips will be removed from both valve leaflets and be extracted entirely from the heart.

The technology of the present invention can be deployed from a left atrial aspect (transseptal or direct atrial access), or from the left ventricular aspect (transapical, direct ventricular puncture, or retrograde aortic access). The cutting action can be provided by a "noose," by a scissor-like device, by a wire-based cutter similar to a "cheese cutter," by a radiofrequency electrode cutting element, or the like. In some instances, the mitral valve clips may be removed from both anterior and posterior leaflets, and a snare, bioptome-type device, or other removal catheter may be used to completely remove the mitral valve clip from the body. The present invention may be used to remove valve clips from tricuspid valves as well as mitral valves, and the catheters be placed through transseptal and transapical guiding catheter which are typically large enough to accommodate all catheters being used in the procedure simultaneously.

Figure 1:
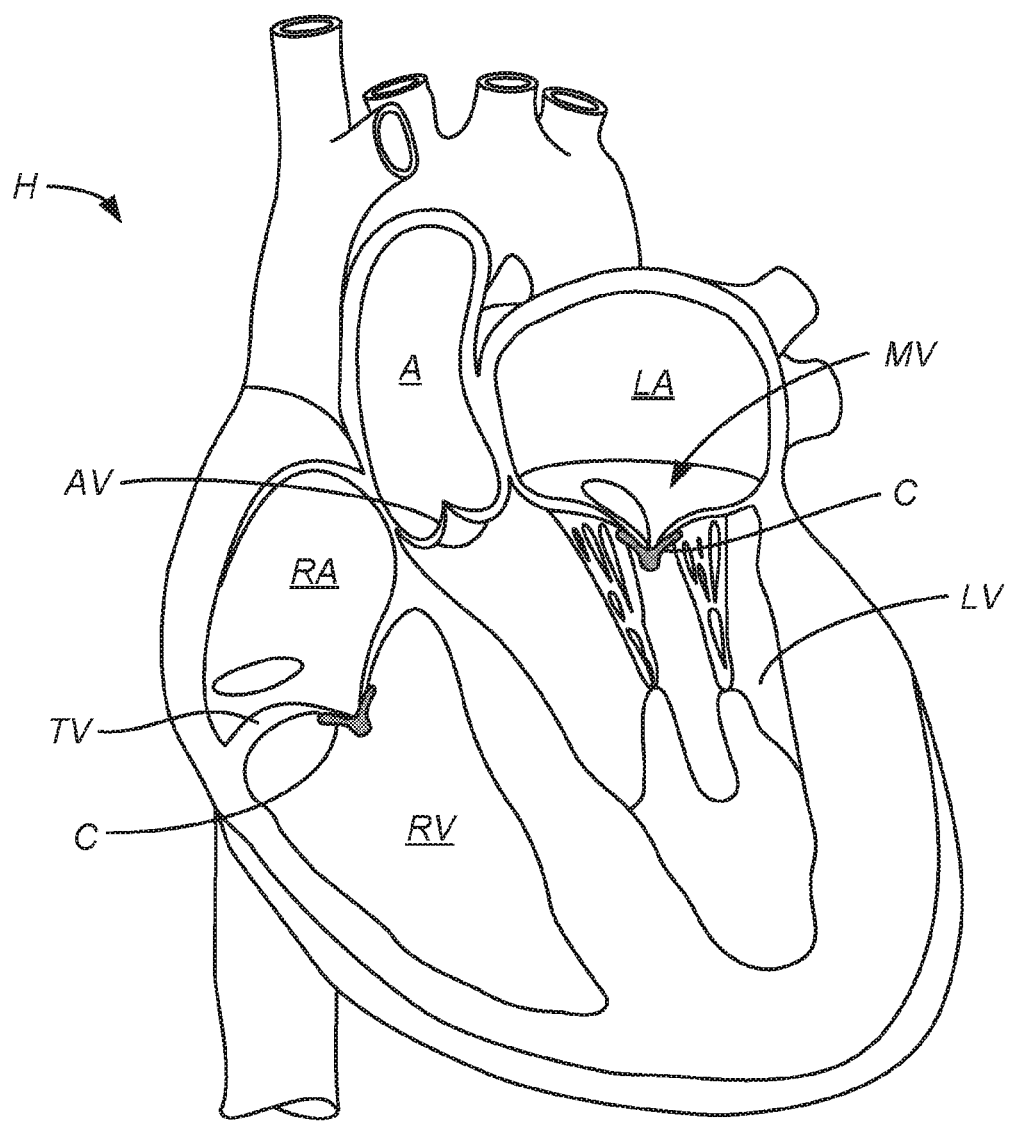
FIGS. 1 and 1A illustrate the anatomy of the mitral valve after implantation of a mitral valve clip.
Figure 1A:
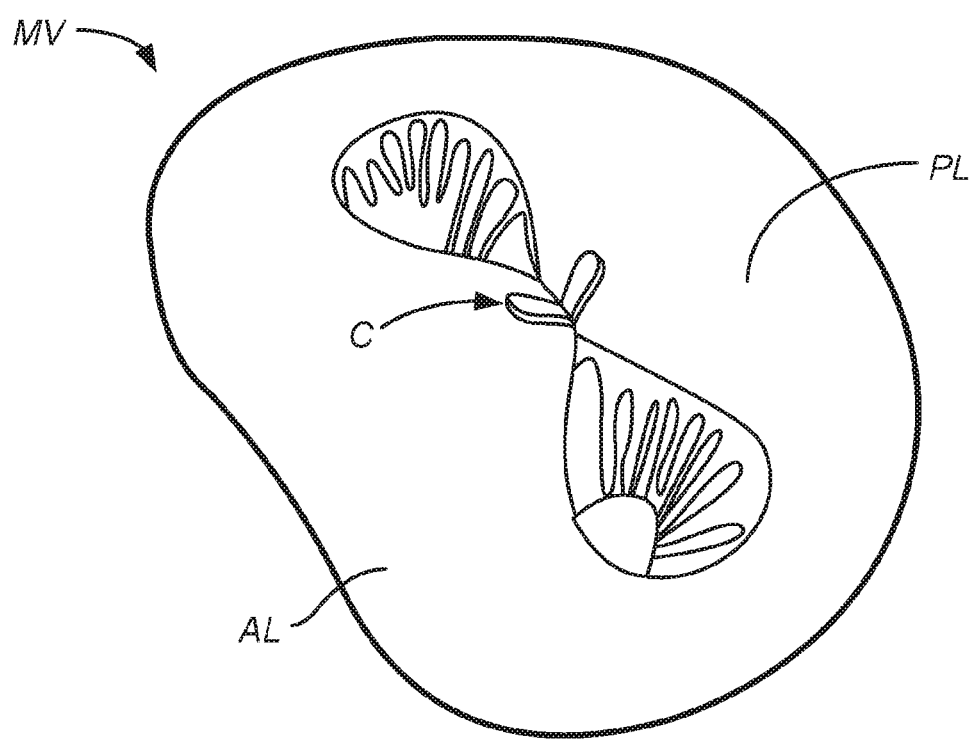

Referring now to FIGS. 1 and 1A, valve clips C may be implanted in the leaflets of a mitral valve MV as well as a tricuspid valve TV in a heart H. The mitral valve MV separates the left atrium LA from the left ventricle LV, and the tricuspid valve TV separates the right atrium RA from the right ventricle RV. For completeness, it is noted that blood flows from the left ventricle LV through the aortic valve AV into the aorta A. As shown in more detail in FIG. 1A, the clip C in the mitral valve MV may be located near a middle of the valve opening between the anterior leaflet AL and the posterior leaflet PL. The clip C, however, could also be implanted at other locations between the leaflets away from the middle of the valve opening.

Referring now to FIGS. 2A and 2B, a capture catheter 10 comprises a shaft 12 having a proximal end 14 and a distal end 16. A control handle 18 is attached to the proximal end of the shaft, and a deflection knob 20 is located at the distal of the handle. The capture catheter 10 will typically also include a flush port 22 and will have a central lumen adapted to receive a guidewire 24 having a shapeable tip 26 at its distal end. As shown in particular FIG. 2B, a distal region 28 of the catheter shaft 12 will be actively deflectable or "steerable" so that the region can be deflected by up to 180°, as shown. Such deflection will be controlled by the deflection knob 20, and suitable deflection mechanisms may include pull wires, slotted regions at the distal end of the shaft, or any other conventional catheter deflection technology.

Figure 3:
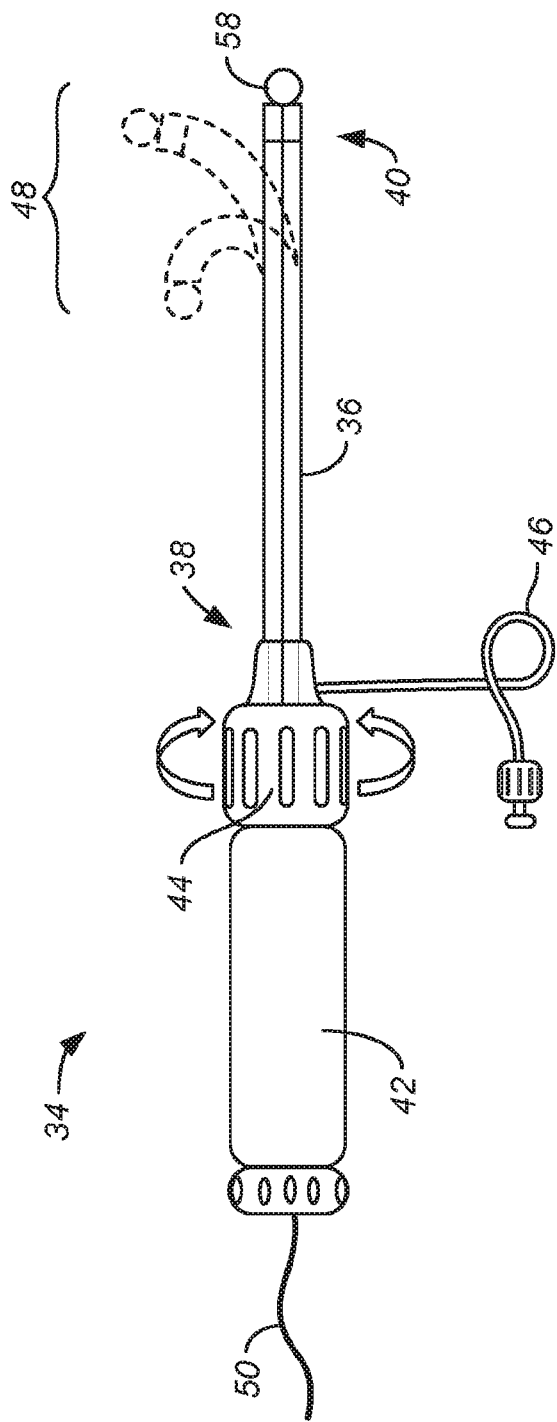
FIG. 3 illustrates a transfer catheter constructed in accordance with the principles of the present invention.

Referring now to FIG. 3, a transfer catheter 34 includes a shaft 36 having a proximal end 38 and a distal end 40. A control handle 42 is attached to the proximal end of the shaft, and a deflection knob 44 is disposed at the distal end of the control handle 42. The transfer catheter 34 may also include a flush port 46 and will typically have a steerable distal tip 48 similar to that described above for the capture catheter 10.

Figure 4:
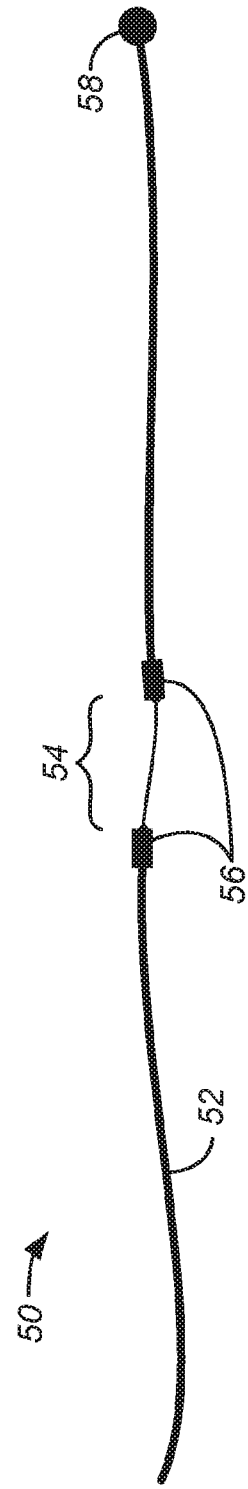
FIG. 4 illustrates a cutting member used with the capture and transfer catheters in the methods of the present invention.

Referring now to FIG. 4, a cutting member 50 comprises an elongate body 52 which typically has a wire-like configuration (typically being electrically conductive in the case of electrosurgical cutting members as described below) so that it may be fed through an advancement lumen of the transfer catheter 34. The cutting member 50 further includes a cutting region 54 which typically spans a region near a middle of the length of the elongate body, typically having a length from 0.5 cm to several centimeters, and which typically is bounded on each side by a radiopaque marker 56. In the case of electrosurgical cutting members, the member may comprise an electrically conductive wire where the cutting region uninsulated and the regions on either side of the cutting region are electrically insulated. A magnetic distal element 58 will typically be located at one end of the elongate body 52 and, as shown in FIG. 3, when the cutting member 50 is loaded onto the transfer catheter 34, the magnetic distal element 58 will extend outwardly from the distal tip 40 of the catheter so that it is exposed and available to magnetically attract the magnetic tip 30 of the capture catheter 10 as described below.

As shown in FIGS. 5A through 5E, the magnetic tip 30 of the capture catheter 10 may take a variety of forms. Magnetic tip 30a (FIG. 5A) has a bullet shape with a through lumen to accommodate the guidewire of the capture catheter. Magnetic tip 30b has a disc-like shape and also has a through lumen to accommodate the guidewire in the capture catheter.

Figure 5A:
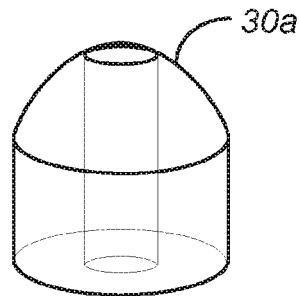
FIGS. 5A through 5E illustrate different embodiments of magnetic tips on the capture catheters and magnetic distal elements on the cutting members.
Figure 5B:
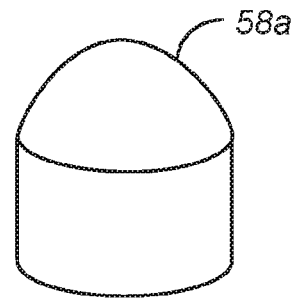
Figure 5C:
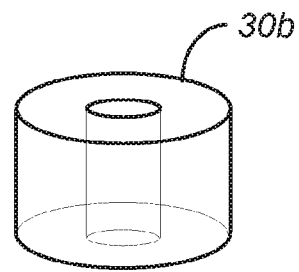
Figure 5D:
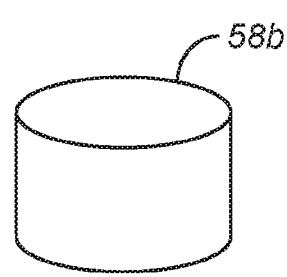
Figure 5E:
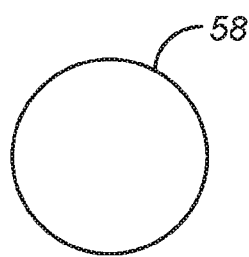

The magnetic distal element 58 of the cutting member 50 may also have a variety of configurations. Most simply, the magnetic distal element 58 will have a sphere shape as shown in FIG. 5E. Alternatively, the magnetic distal element may have a bullet shape 58a as shown in FIG. 5B or a disc-like shape 58b as shown in FIG. 5D.

Figure 6:
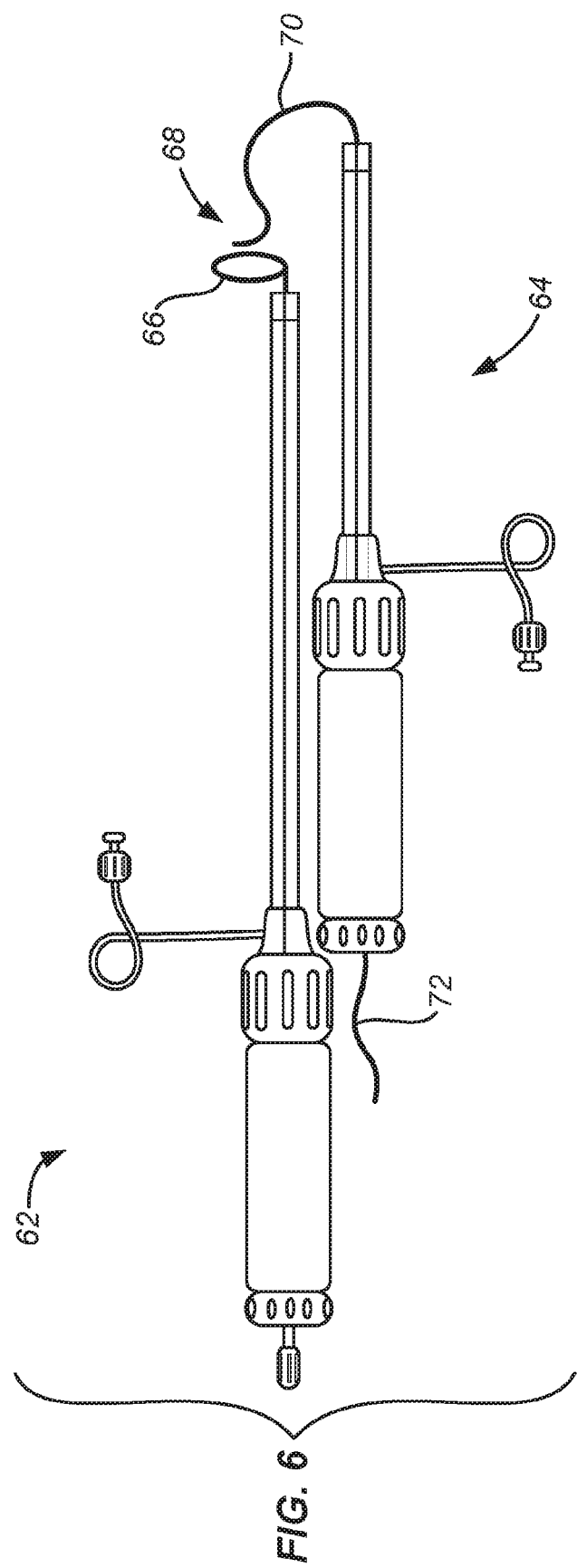
FIG. 6 illustrates an alternative system according to the present invention including a capture catheter having a capture loop at its distal end.

As described thus far, the capture catheter 10 and the cutting member 50 will each have magnetic elements to allow capture of the cutting member by the capture catheter 50. While this is a preferred design, a variety of other capture mechanisms could also be employed. For example, as shown in FIG. 6, a capture catheter 62 may carry a capture loop 66 at its distal end. The capture loop could be used then to capture a free end 70 of a cutting member 72 carried by transfer catheter 64. The use of hooks, barbs, coil targets, and the like, would also be possible to allow for capture of the cutting member by a capture catheter.

Referring now to FIGS. 7A through 7F, the use of capture catheter 10 and transfer catheter 34 for removing a pair of clips C1 and C2 from a mitral valve MV via a transseptal approach will be described. A steerable distal tip 28 of guidewire 24 is first introduced through a transseptal sheath 74 into a left atrium above the mitral valve. The tip 28 can be advanced between the clips C1 and C2 under fluoroscopic guidance with the heart beating. Optionally, the capture catheter 10 could be used to assist in placing the guide wire 24 between the clips before the catheter 10 is the advanced over the guide wire. The guide wire can be passive or active.

Figure 7A:
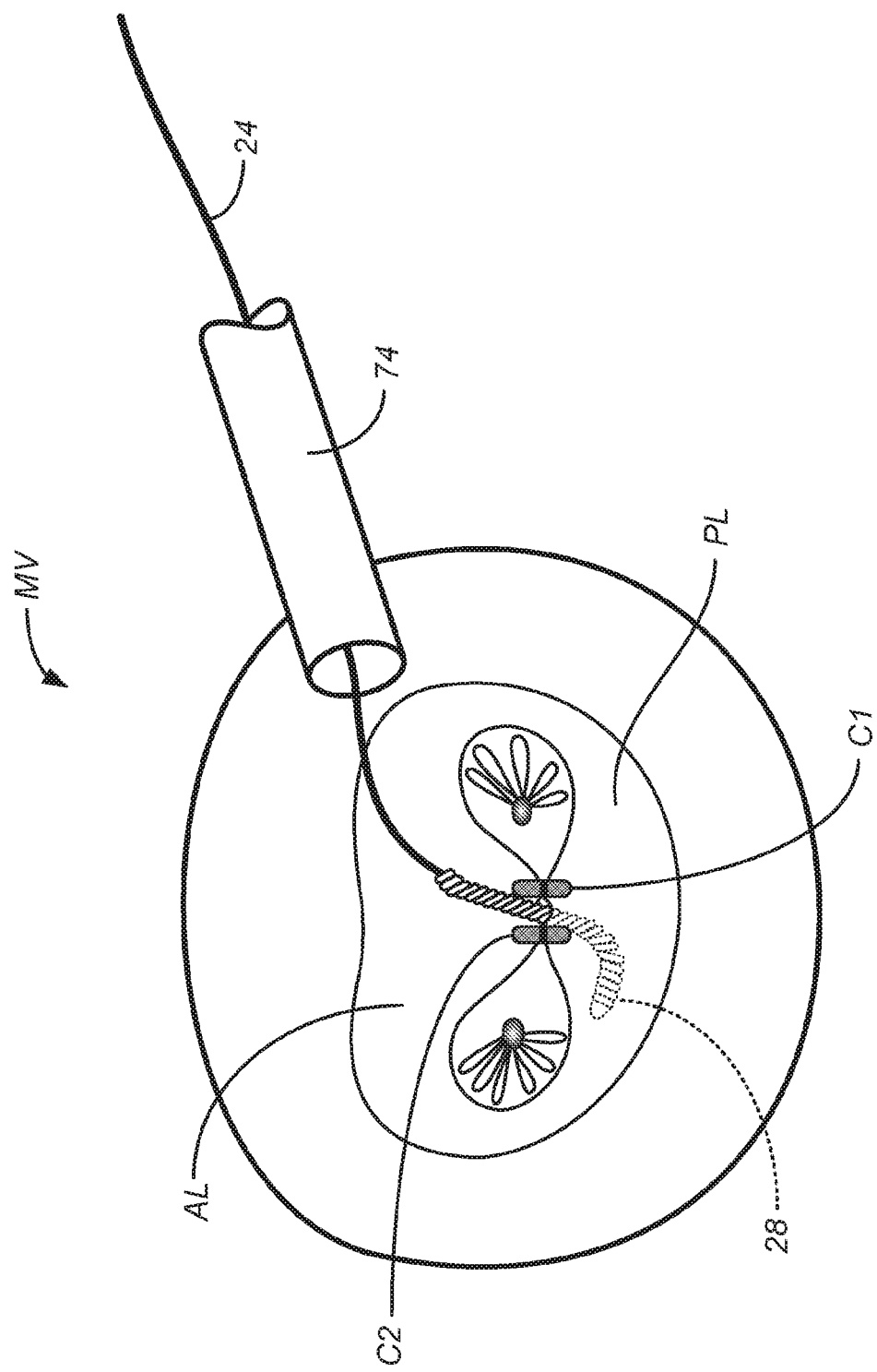
FIGS. 7A through 7F illustrate use of a capture catheter and a transfer catheter in a method for removing a pair of clips implanted in a mitral valve in accordance with the principles of the present invention.
Figure 7B:
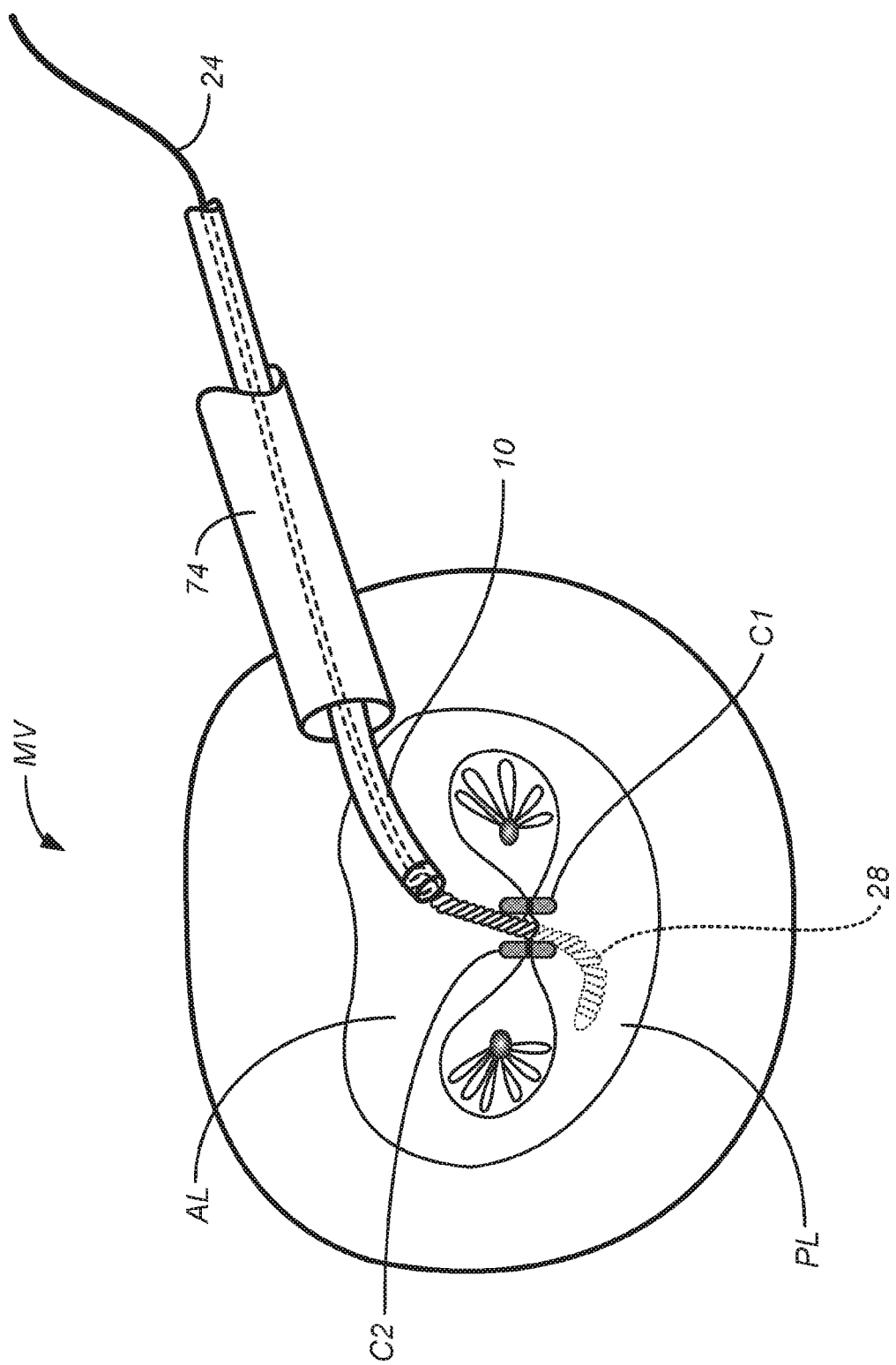
Figure 7C:
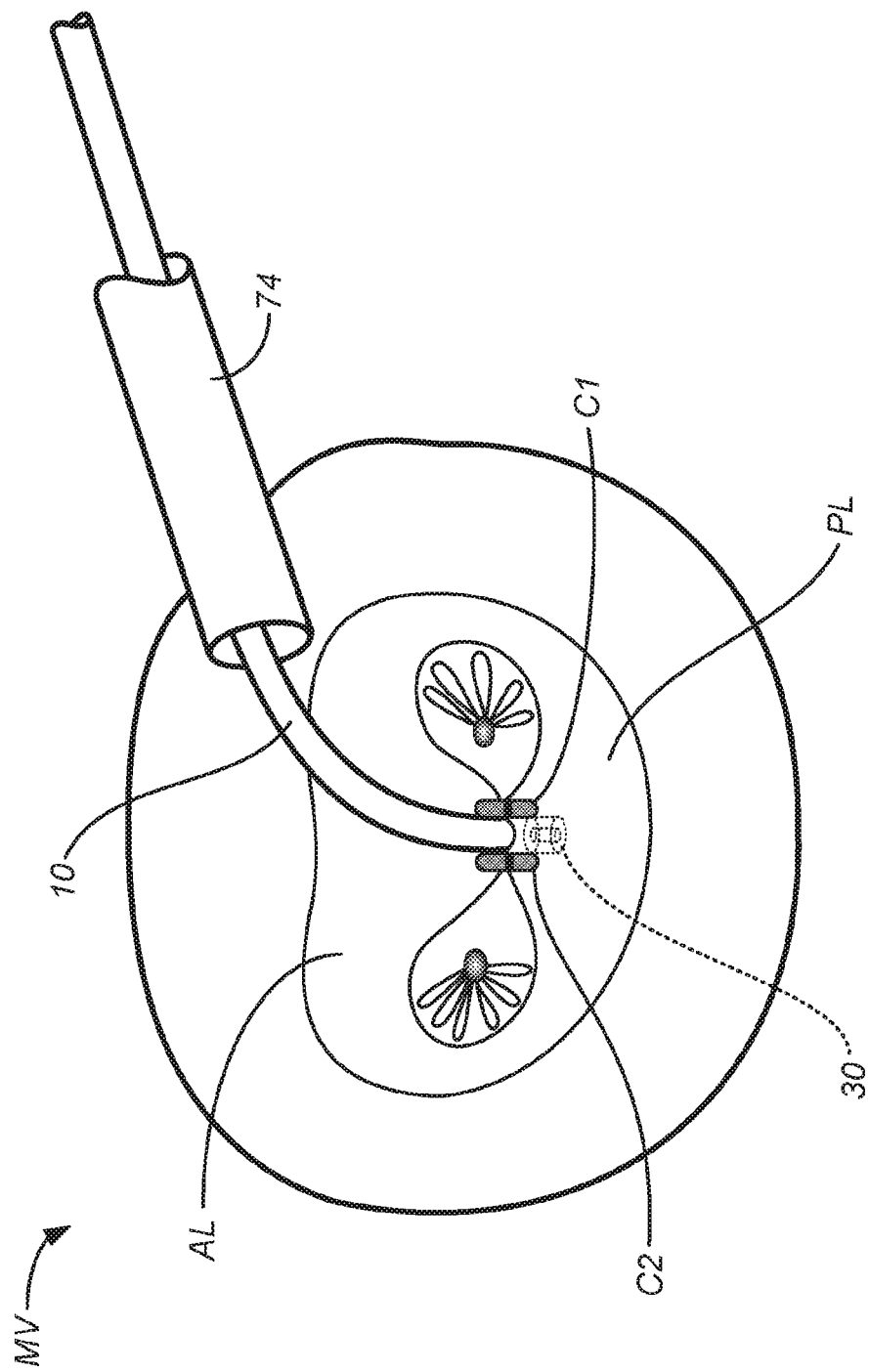
Figure 7D:
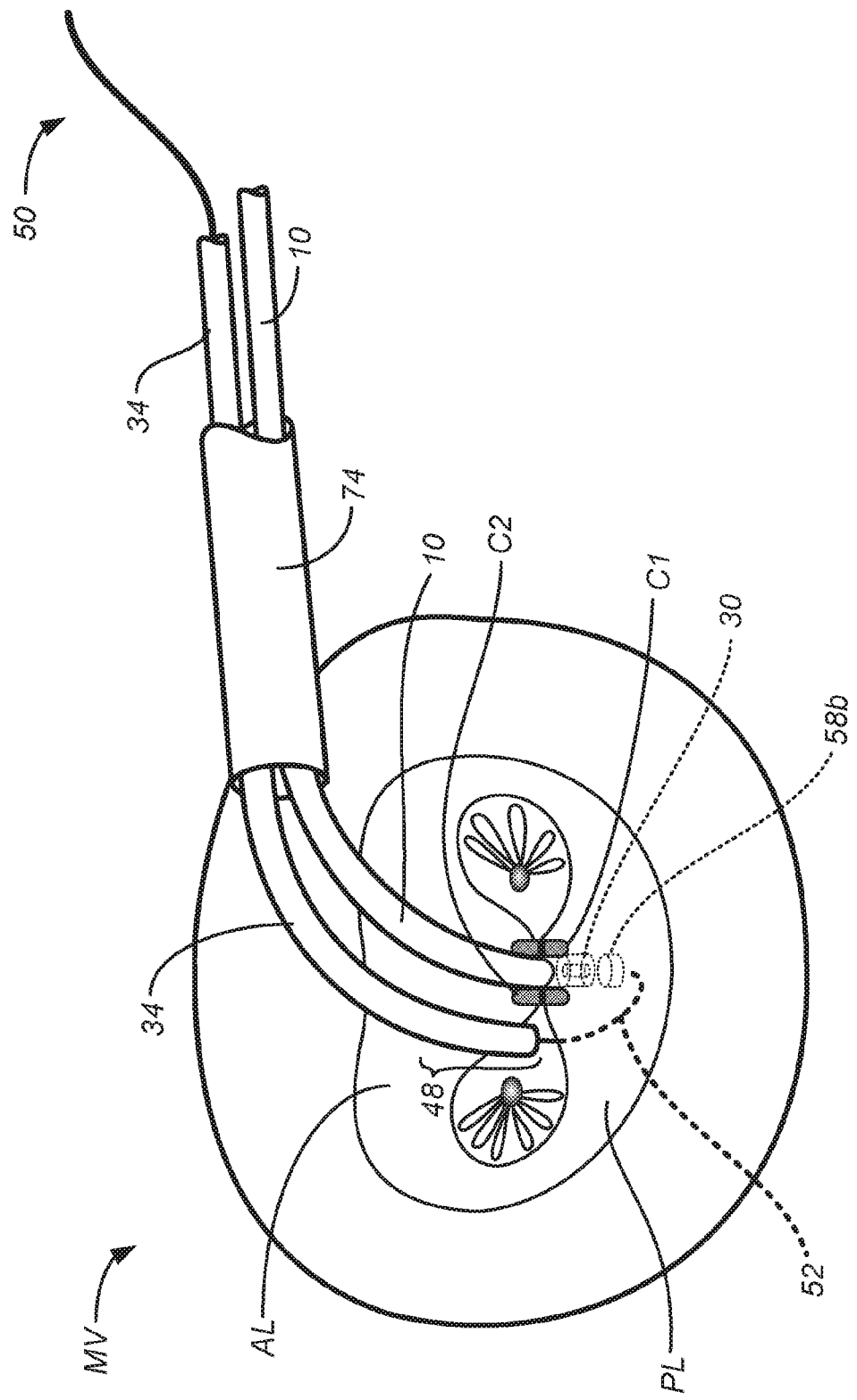

After the guidewire is placed, as shown in FIG. 7A, the capture catheter 10 can be advanced over the guidewire 24 so that it is positioned above the clips C1 and C2, as shown in FIG. 7B. The distal end of the capture catheter 10 is then advanced between the clips C1 and C2 so that the magnetic tip enters the left ventricle, as shown in FIG. 7C. The transfer catheter 34 may then be introduced through the transseptal sheath 74 in parallel to the capture catheter 10 and steered to advance the magnetic distal element 58b on the cutting member 50 so that it engages the magnetic tip 30 on the capture catheter 10. For example, the steerable distal region 48 of the transfer catheter 34 can be advanced downwardly between the anterior leaflet AL and posterior leaflet PL and manipulated to engage the magnetic distal element 58b against the magnetic tip 30.

Figure 7E:
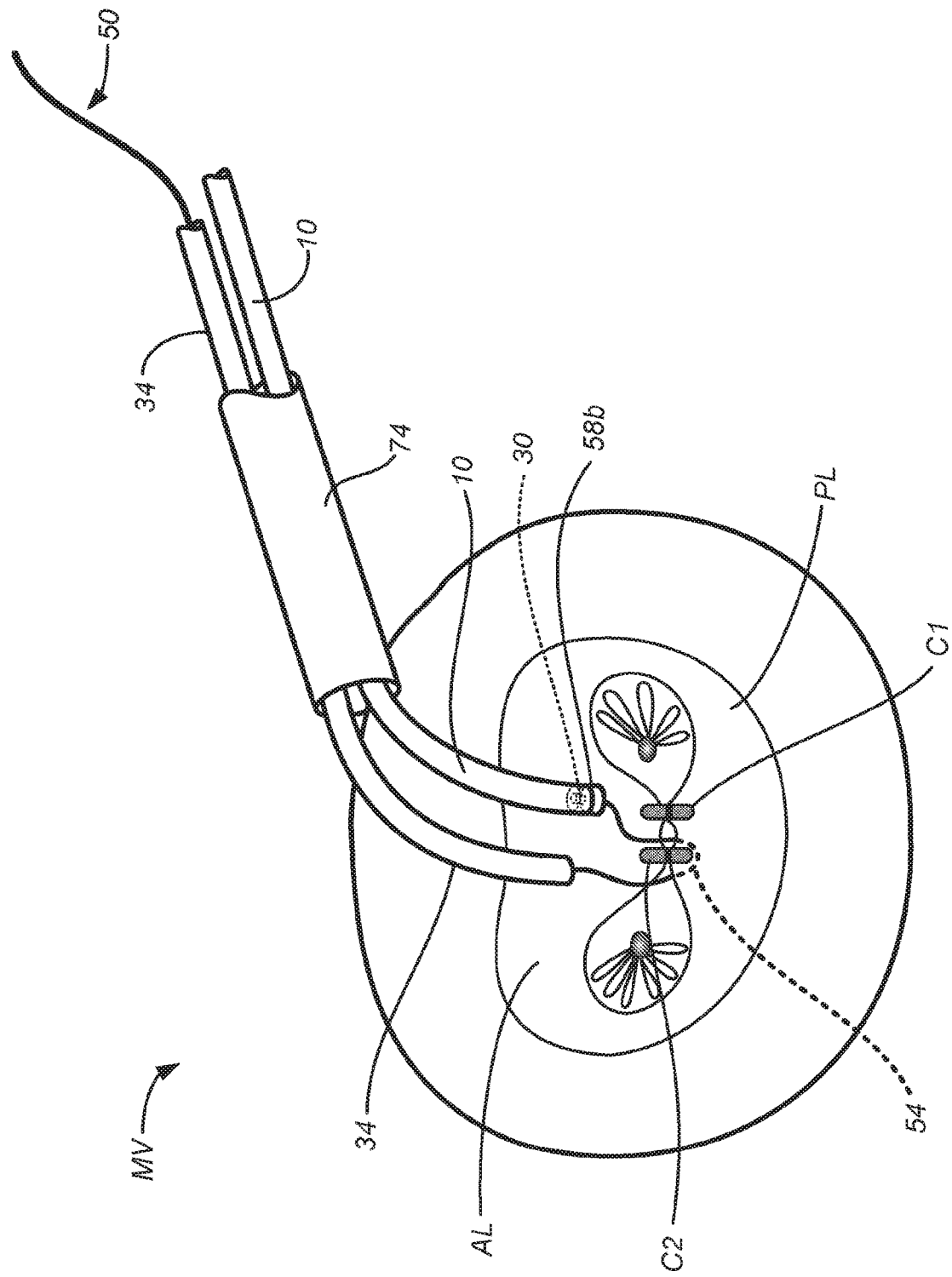
Figure 7F:
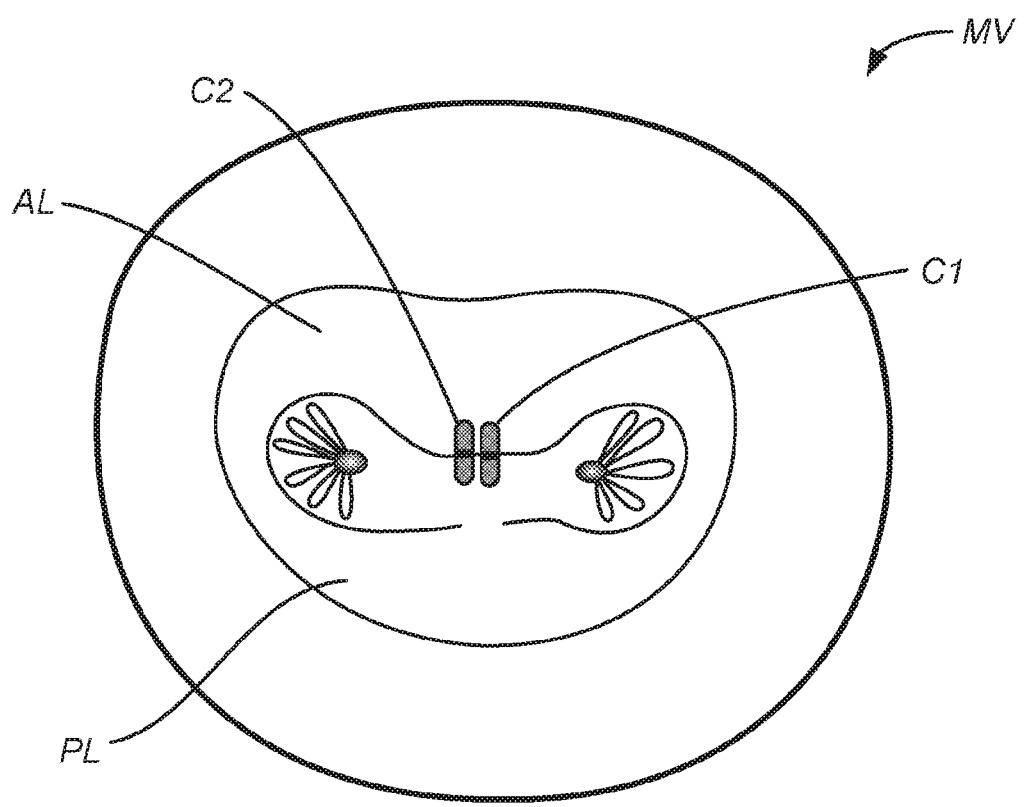

After the cutting member 50 and capture catheter 10 are coupled together, the capture catheter 10 may be pulled back to expose the cutting region 54, and the catheters manipulated to engage the cutting region 54 against the second valve clip C2, as shown in FIG. 7E. The cutting region 54 can then be manipulated to saw through or electrode surgically cut the tissue of the posterior leaflet PL surrounding the clip C2. The procedure may then be repeated to excise the first clip C1 from the posterior leaflet PL, as shown in FIG. 7F, resulting in opening of the mitral valve to allow a prosthetic valve implantation or other intervention to take place. While excision of the posterior leaflet is illustrated in FIGS. 7A-7F, in some instances it would be preferable to excise the anterior leaflet tissue leaving the clip(s) attached to the posterior leaflet.

Figure 8:
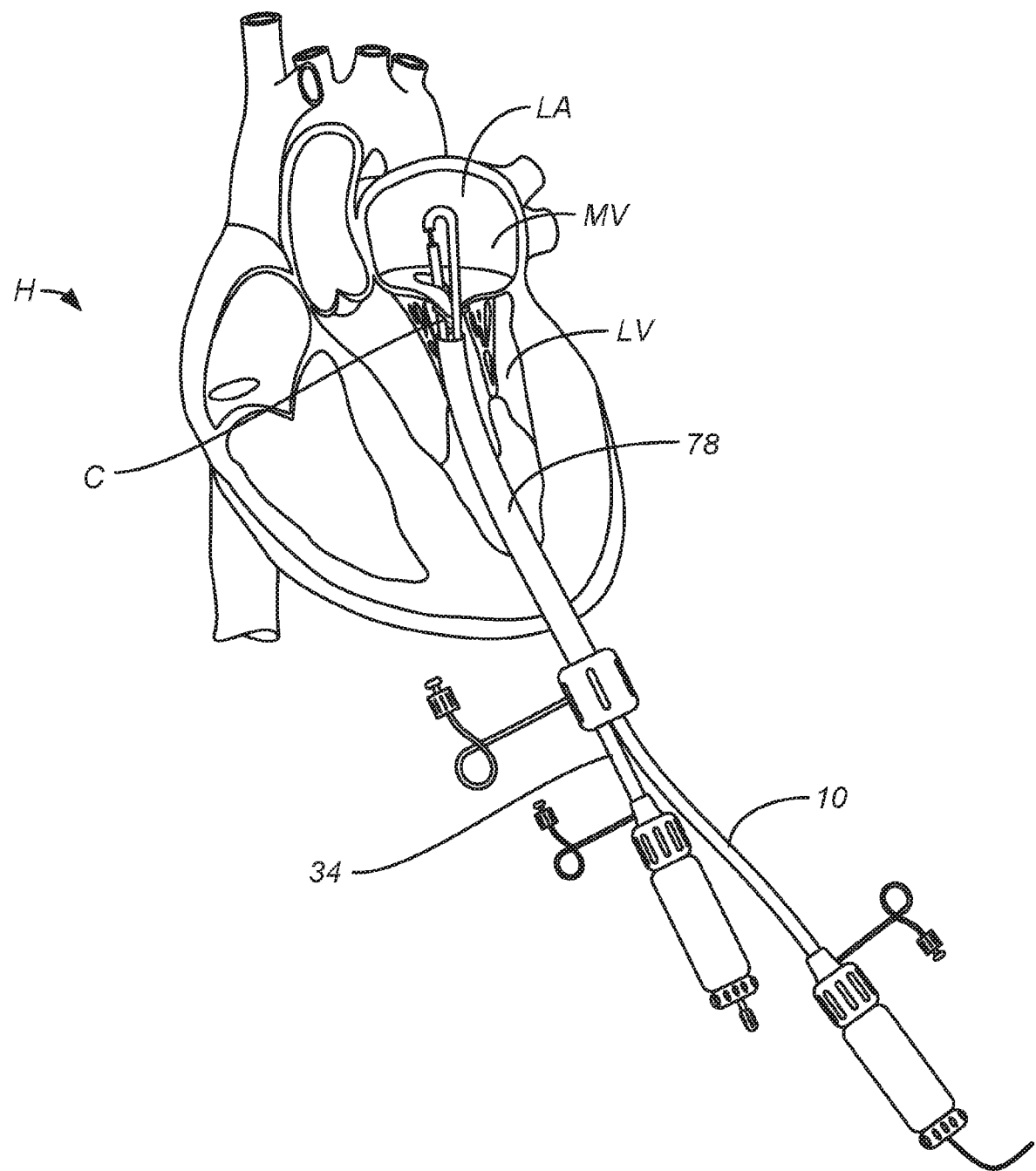
FIG. 8 illustrates transapical introduction of a capture catheter and a transfer catheter into a left atrium for excising a valve clip in a mitral valve in accordance with the principles of the present invention.

Referring now to FIG. 8, excision of valve clip C from the mitral valve MV can also be performed using capture catheter 10 and transfer catheter 34 through a transapical sheath 78. Using the transapical approach, the distal tips of the catheters 10 and 34 will be advanced upwardly from the left ventricle LV to the left atrium LA, and the tissue can then be excised using the catheters as generally as described previously.

Figure 9A:
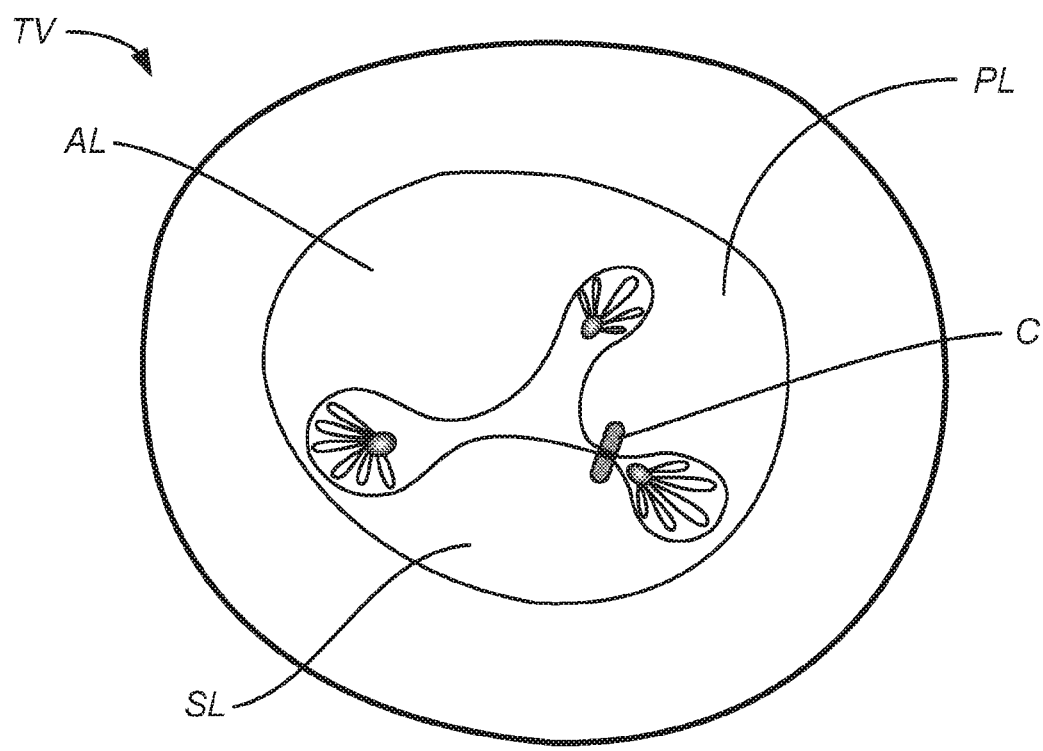
FIGS. 9A through 9C illustrate use of a capture catheter and a transfer catheter in a method for removing a valve clip from a tricuspid valve in accordance with the principles of the present invention.
Figure 9B:
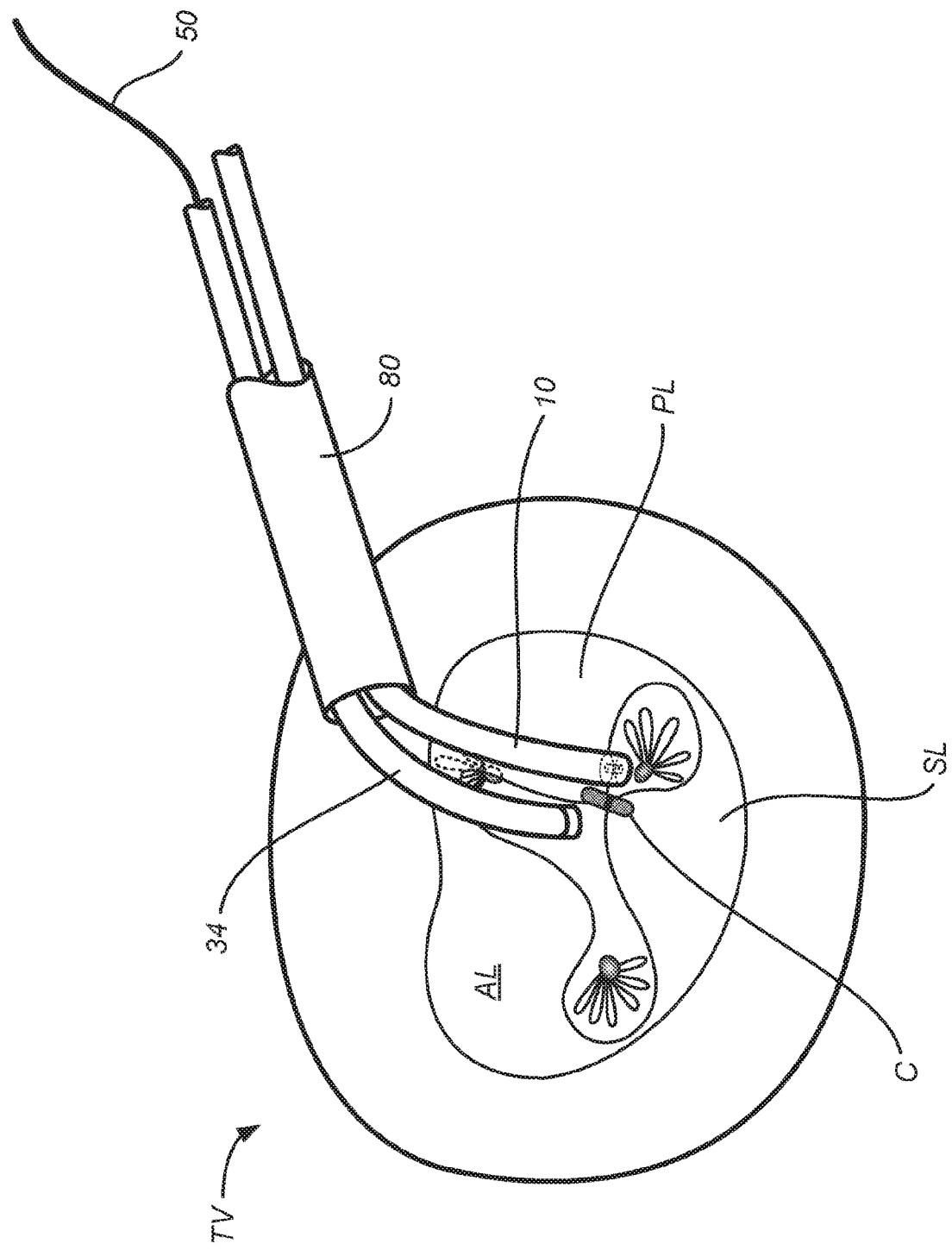
Figure 9C:
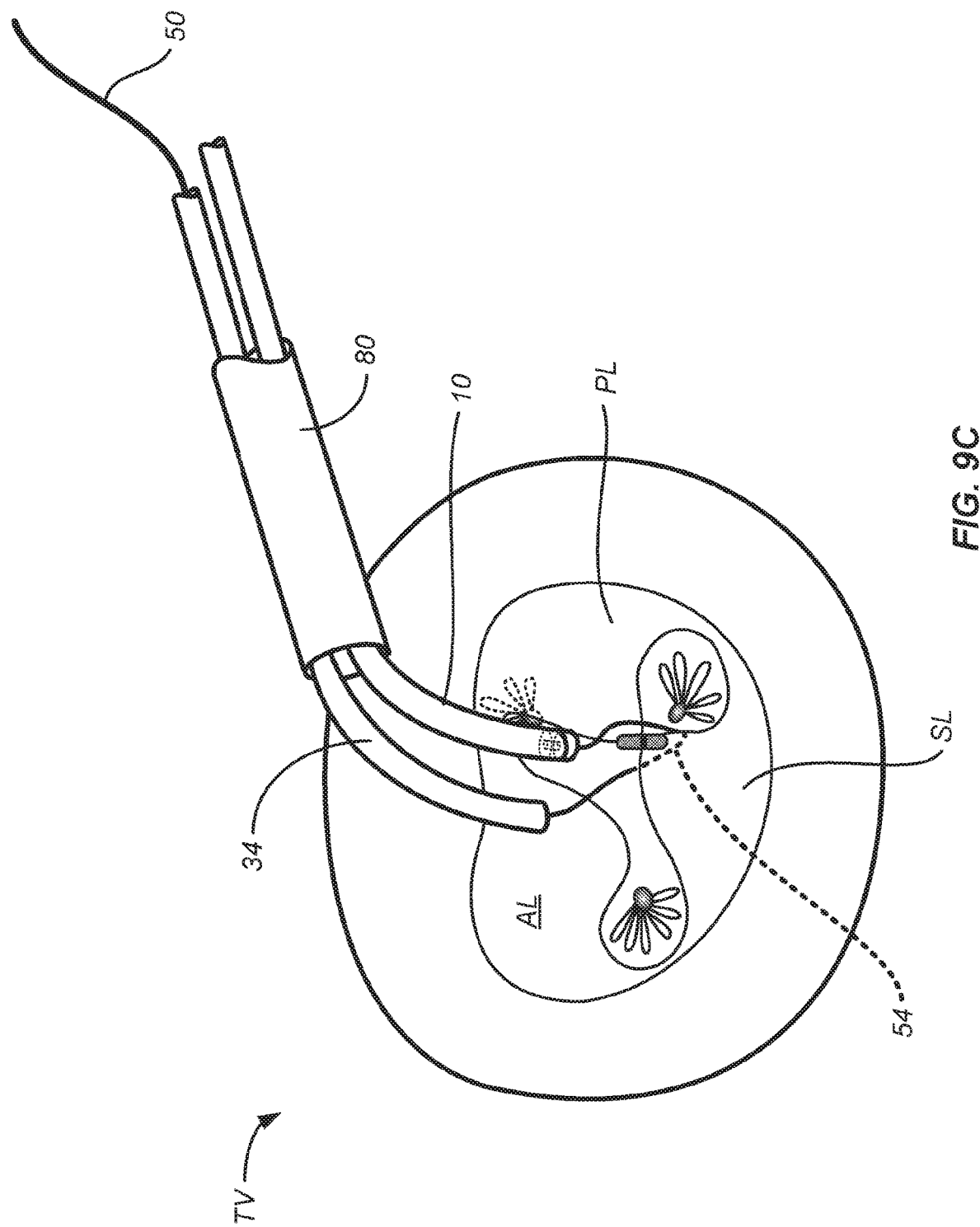

Referring now to FIGS. 9A through 9C, excision of a valve clip C implanted between an anterior leaflet AL and a septal leaflet SL in a tricuspid valve TV will be described. Capture catheter 10 and transfer catheter 34 can be introduced through an access sheath 80 into the right atrium above the tricuspid valve, as shown in FIG. 9B. The catheters 10 and 34 can be used to position the cutting region 54 of the cutting member 50 on a side of the clip C in the septal leaflet SL as shown in FIG. 9C. The cutting member 50 can then be manipulated in any of the ways described previously to excise the tissue of the septal leaflet SL to release the clip C and open the tricuspid valve, as shown in FIG. 9C. The portion of the clip C implanted in the anterior leaflet can also be excised, or the clip can be left in place, prior to performing a subsequent intervention on the valve.

Figure 10A:
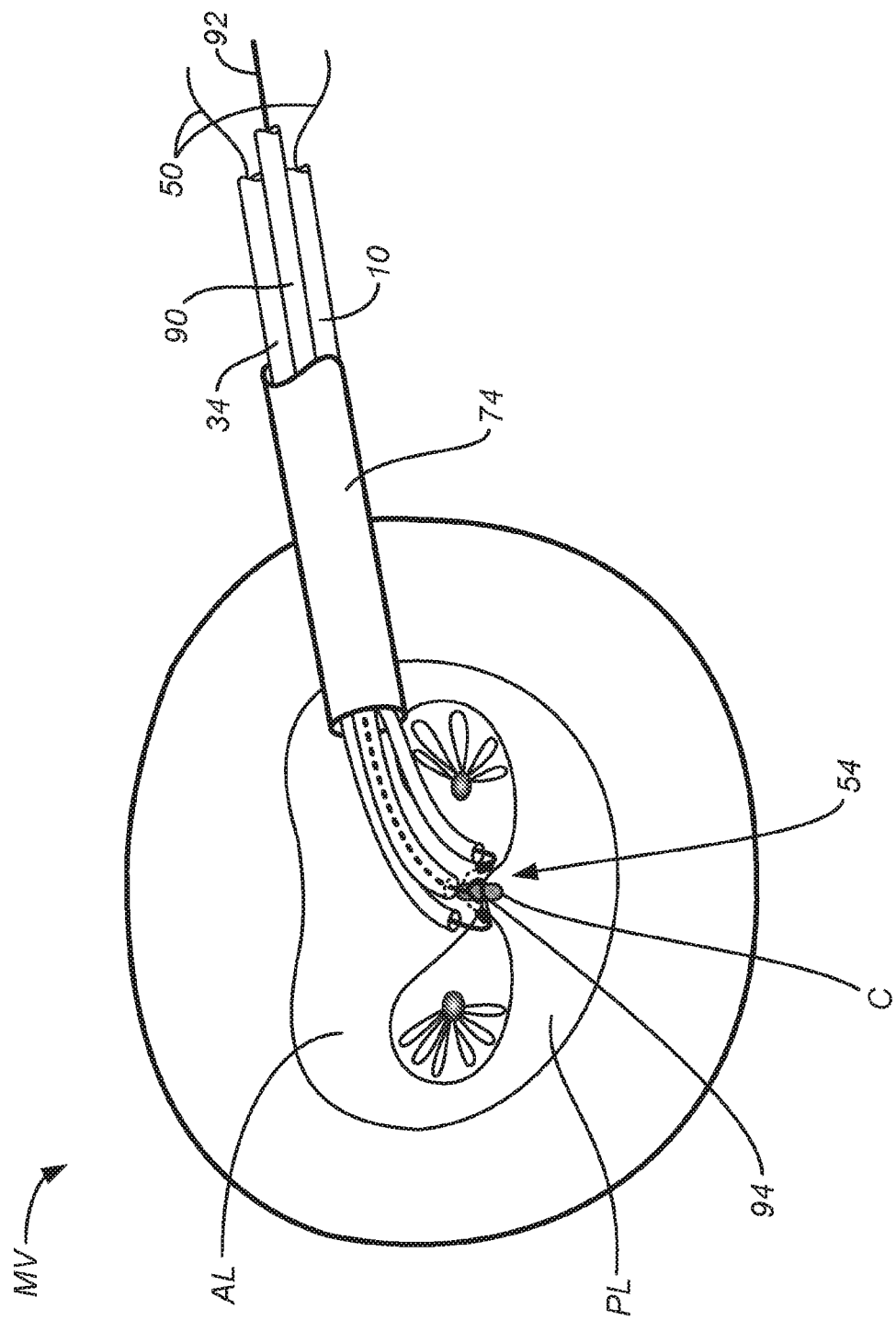
FIGS. 10A through 10E illustrate use of a capture catheter and a transfer catheter in a method for removing a single valve clip from a mitral valve in accordance with the principles of the present invention.
Figure 10B:
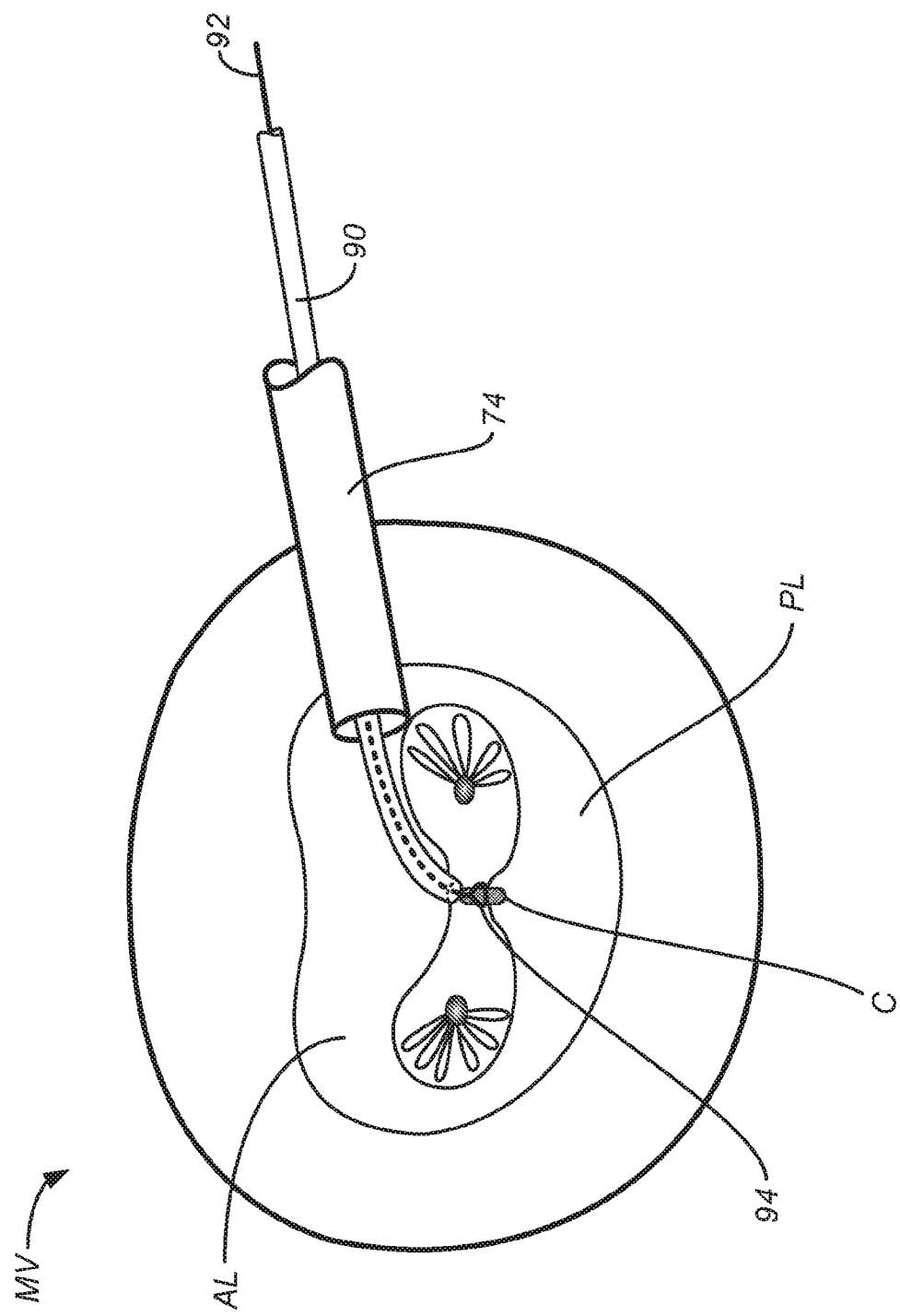
Figure 10C:
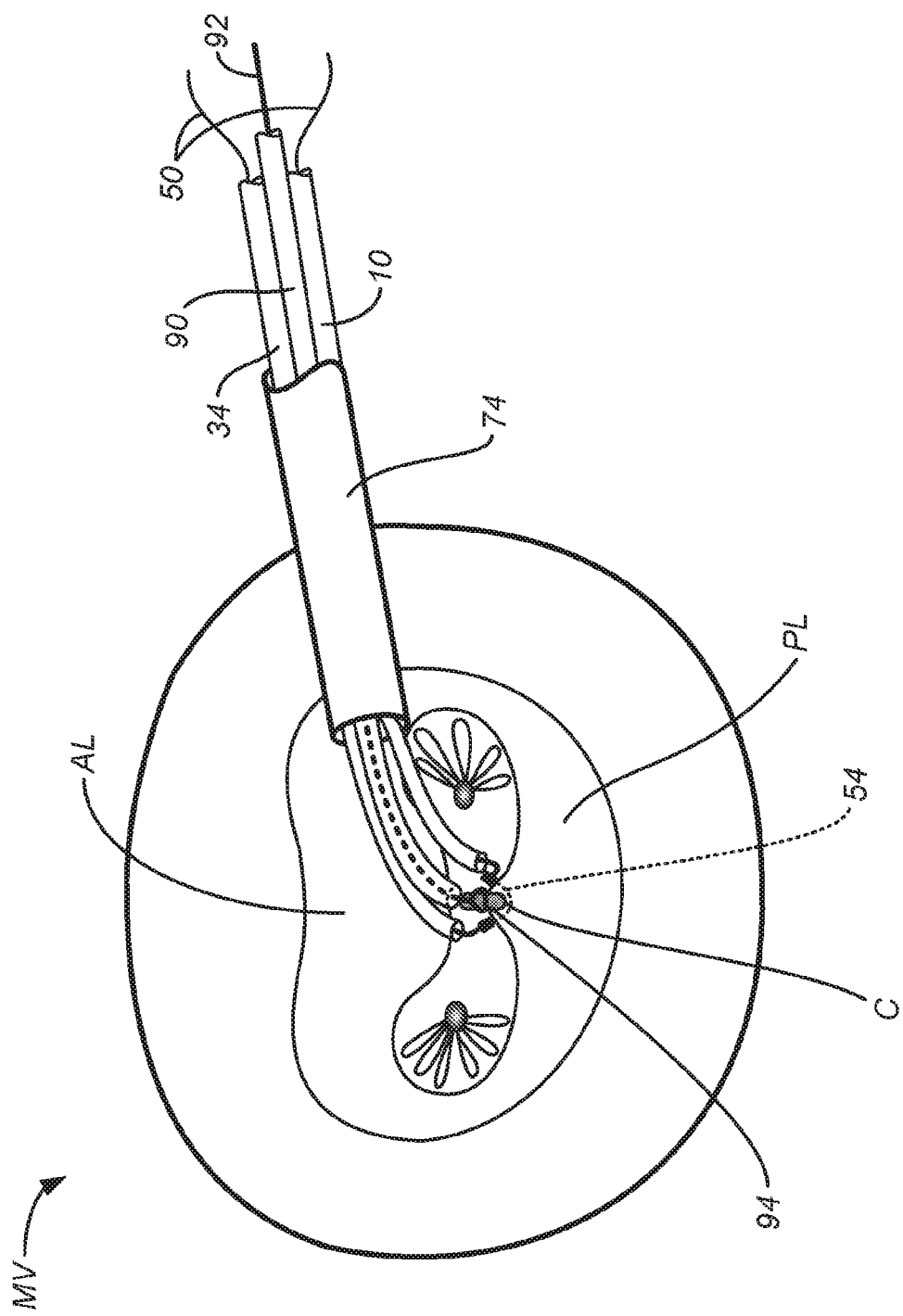
Figure 10D:
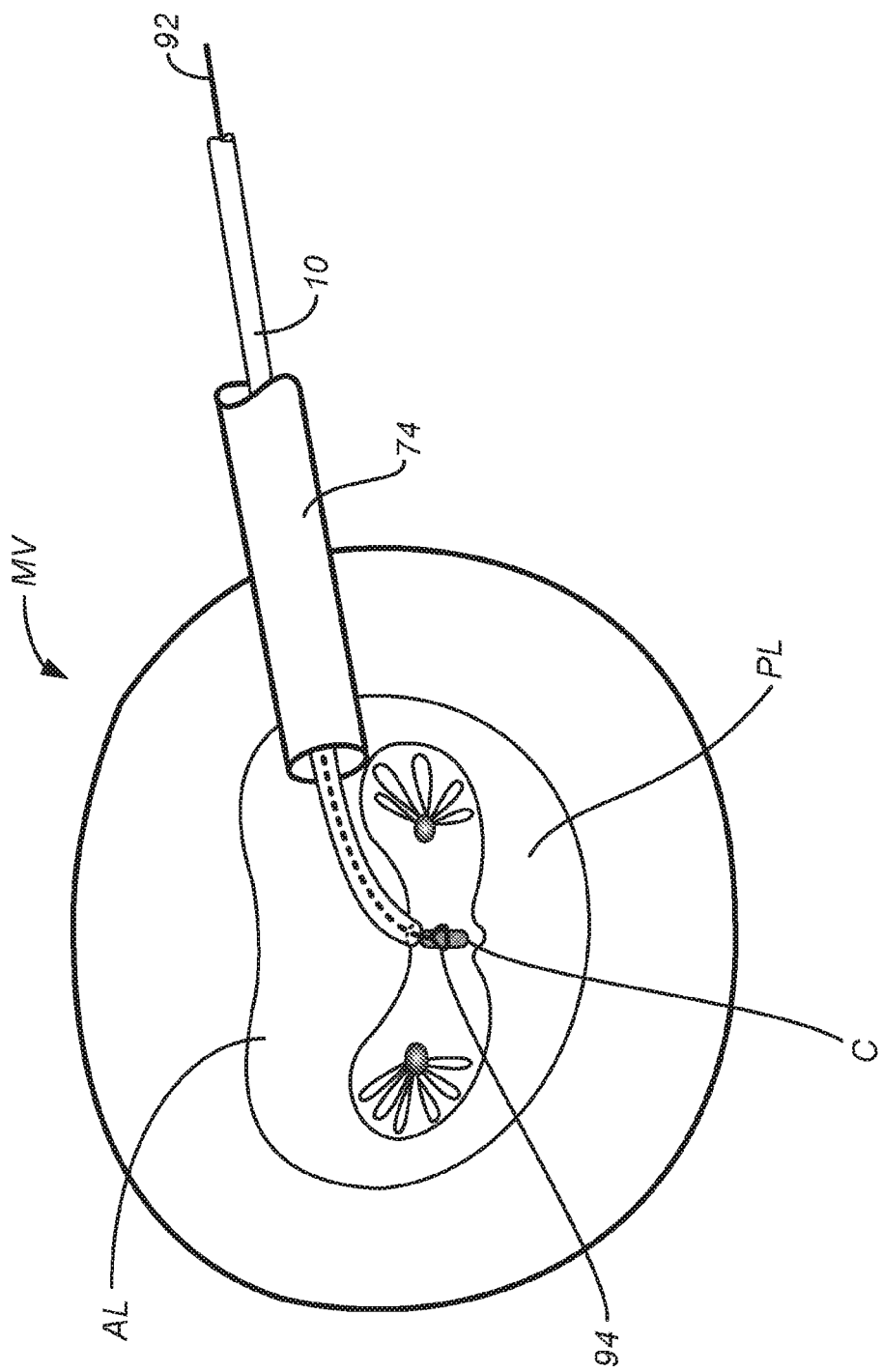
Figure 10E:
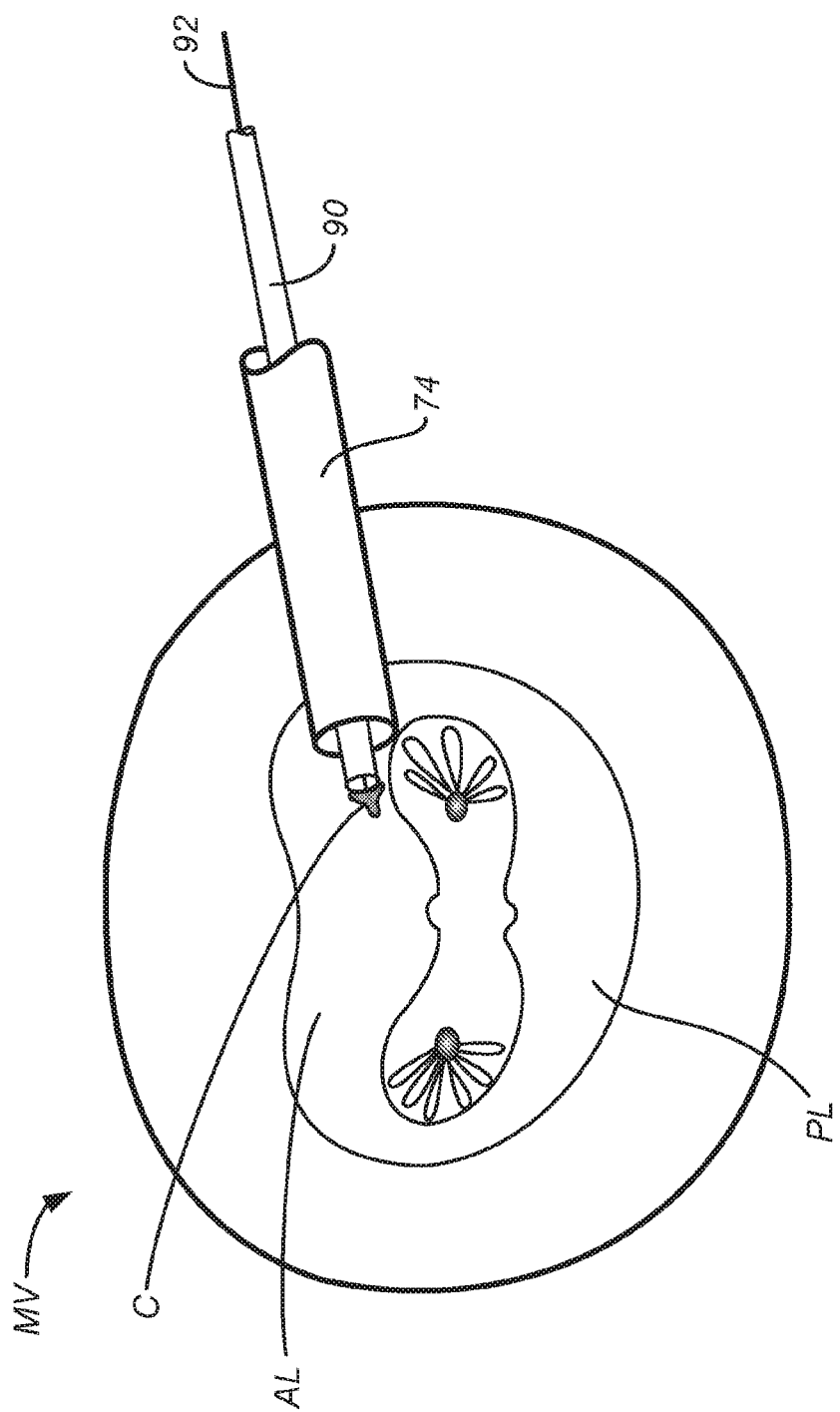

Referring now to FIGS. 10A through 10E, a single valve clip C can be removed from a mitral valve MV by introducing the capture catheter 10 and the transfer catheter 34 into the left atrium using a transseptal sheath 74, as generally described previously. In addition, a clip removal catheter 90 can be introduced through the transseptal sheath 74 simultaneously with the capture catheter 10 and the transfer catheter 34 in order to engage and stabilize the clip C. As shown in FIG. 10A, a clip capture element 94 at the distal end of a manipulation wire 92 can be delivered through a lumen of the clip removal catheter 90 to capture an upper surface of the clip C. The cutting region 54 of the cutting number 50 is then used to excise the tissue in the anterior leaflet AL, while the clip remains held and stabilized by the clip removal catheter 90, thus freeing the clip from the anterior leaflet, as shown in FIG. 10B (where the capture catheter 10 and transfer catheter 34 are removed for ease of illustration). The capture catheter 34 and transfer catheter 10 may then be repositioned, as shown in FIG. 10C, so that the cutting region 54 of the cutting member 50 is positioned against the posterior leaflet PL, and the cutting region can then be manipulated to excise tissue in the posterior leaflet to release the clip, as shown in FIG. 10D. The clip removal catheter 90, which continues to hold the clip C, can be then be used to withdraw the clip C from the mitral valve, as shown in FIG. 10E. The mitral valve MV is then completely free from implanted clips to receive a mitral valve prosthesis or to have another corrective intervention performed.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. A system for excising an implanted clip approximating opposed valve leaflets in a heart valve, said system comprising:
a capture catheter configured to be introduced into a heart chamber adjacent to the valve leaflets on one side of the clip;
a transfer catheter configured to be introduced into the heart chamber adjacent to the valve leaflets on another side of the clip; and
a cutting member configured to be deployed from the transfer catheter to the capture catheter to place the cutting member against tissue of at least one of the valve leaflets to excise the clip, wherein the cutting member comprises a cutting zone formed of an uninsulated conductive member bounded by a first radiopaque marker and a second radiopaque marker.

2. A system as in claim 1, wherein at least one of the capture catheter and the transfer catheter has a steerable distal tip.

3. A system as in claim 1, wherein each of the capture catheter and the transfer catheter has a steerable distal tip.

4. A system as in claim 1, wherein the capture catheter has a magnetic distal tip.

5. A system as in claim 4, wherein the cutting member is carried by the transfer catheter and has a magnetic element exposed at a distal end of the transfer catheter so that manipulation of the transfer catheter positions within the heart chamber allows the capture catheter to capture the cutting member.

6. A system as in claim 4, wherein the magnetic distal tip has one of a sphere shape, a bullet shape, or a disc-like shape.

7. A system as in claim 1, further comprising a clip removal catheter having a distal end configured to engage and capture the clip.

8. A system as in claim 1, wherein the cutting member comprises a radiofrequency electrode for energized cutting of valve tissue.

9. A system as in claim 1, wherein the cutting member comprises a mechanically abrasive or sharpened edge for mechanically cutting valve tissue.

10. A system as in claim 1, further comprising a delivery sheath configured to introduce the capture catheter and the transfer catheter to the heart chamber.

11. A system as in claim 1, wherein a delivery sheath has a lumen sized to simultaneously accommodate both the capture catheter and the transfer catheter.

12. A system as in claim 1, wherein a delivery sheath comprises a transseptal sheath.

13. A system as in claim 1, wherein a delivery sheath comprises a transapical sheath.

14. A system for excising an implanted clip approximating opposed valve leaflets in a heart valve, said system comprising:
 a capture catheter configured to be introduced into a heart chamber adjacent to the valve leaflets on one side of the clip, the capture catheter comprising a magnetic tip;
 a transfer catheter configured to be introduced into the heart chamber adjacent to the valve leaflets on another side of the clip; and
 a cutting member configured to be deployed from the transfer catheter to the capture catheter to place the cutting member against tissue of at least one of the valve leaflets to excise the clip, the cutting member comprising a magnetic element exposed at a distal end of the transfer catheter during delivery so that manipulation of the transfer catheter positions the magnetic element within the heart chamber and allows magnetic attraction of the magnetic tip and the magnetic element so the capture catheter contacts a portion of the cutting member, wherein the cutting member comprises a cutting zone formed of uninsulated conductive member and bounded by a first radiopaque marker and a second radiopaque marker.

15. A system as in claim 14, further comprising a transseptal sheath configured to receive the capture catheter and the transfer catheter.

16. A system as in claim 15, wherein the cutting zone includes a radiofrequency electrode, an abrasive region, or a sharpened edge for cutting valve tissue.

17. A system as in claim 16, further comprising a guidewire with a shapeable tip, the capture catheter being configured to be advanced along the guidewire to the heart chamber.

18. A system as in claim 17, further comprising a clip removal catheter configured to be introduced into a heart chamber adjacent to the valve leaflets.

19. A system as in claim 18, further comprising a clip capture element configured to be selectively delivered through a lumen of the clip removal catheter to capture the clip.

20. A system for excising an implanted clip approximating opposed valve leaflets in a heart valve, said system comprising:
 a capture catheter configured to be introduced into a heart chamber adjacent to the valve leaflets on one side of the clip;
 a transfer catheter configured to be introduced into the heart chamber adjacent to the valve leaflets on another side of the clip; and
 a cutting member configured to be deployed from the transfer catheter to the capture catheter to place the cutting member against tissue of at least one of the valve leaflets to excise the clip, wherein the cutting member comprising at least one selected from a group of a sharpened member, an abrasive member, and an RF electrode member, wherein the cutting member comprises an elongate cutting zone formed of an uninsulated conductive member proximate a distal end of the cutting member, the cutting zone bounded by a first radiopaque marker and a second radiopaque marker.

21. A system as in claim 20, wherein the cutting zone is located near a middle portion of the cutting member.

* * * * *